US010724991B2

(12) United States Patent
Murase et al.

(10) Patent No.: US 10,724,991 B2
(45) Date of Patent: Jul. 28, 2020

(54) PARTICULATE SENSOR

(71) Applicant: NGK Spark Plug Co., LTD., Nagoya (JP)

(72) Inventors: Hirokazu Murase, Nisshin (JP); Takeshi Sugiyama, Ichinomiya (JP); Toshiya Matsuoka, Kaizu (JP)

(73) Assignee: NGK Spark Plug Co., LTD., Nagoya (JP)

(*) Notice: Subject to any disclaimer, the term of this patent is extended or adjusted under 35 U.S.C. 154(b) by 448 days.

(21) Appl. No.: 15/598,715

(22) Filed: May 18, 2017

(65) Prior Publication Data
US 2017/0343511 A1    Nov. 30, 2017

(30) Foreign Application Priority Data

May 24, 2016   (JP) ................................. 2016-103466

(51) Int. Cl.
*G01N 27/70*       (2006.01)
*G01N 15/06*       (2006.01)
(Continued)

(52) U.S. Cl.
CPC ........... *G01N 27/70* (2013.01); *F01N 11/007* (2013.01); *G01N 15/0656* (2013.01);
(Continued)

(58) Field of Classification Search
CPC ..................................................... G01N 27/70
(Continued)

(56) References Cited

U.S. PATENT DOCUMENTS

2012/0285219 A1*  11/2012  Matuoka ............. F02D 41/1466
                                                      73/23.33
2014/0145724 A1*   5/2014  Shinada ................. G01N 30/64
                                                      324/464
(Continued)

FOREIGN PATENT DOCUMENTS

JP    2015-129712 A    7/2015
JP    2015-163897 A    9/2015
(Continued)

OTHER PUBLICATIONS

Japanese Office Action dated Aug. 6, 2019 for the corresponding Japanese Patent Application No. 2016-103466.

*Primary Examiner* — Walter L Lindsay, Jr.
*Assistant Examiner* — Philipmarcus T Fadul
(74) *Attorney, Agent, or Firm* — Leason Ellis LLP

(57) ABSTRACT

A particulate sensor can reduce the amount of floating ions discharged from the interior of a gas introduction pipe to the outside through a gas discharge opening, without providing an auxiliary electrode member which applies to the floating ions a repulsive force toward the gas introduction pipe to thereby assist the collection of the floating ions by the gas introduction pipe. The particulate sensor has an collection member which is connected to a gas introduction pipe to thereby be maintained at a collection potential and is disposed in the interior of the gas introduction pipe to be located between a forward end of the discharge electrode member and a gas discharge opening such that the forward end of the discharge electrode member cannot be visually recognized from the outside of the gas introduction pipe through the gas discharge opening.

10 Claims, 13 Drawing Sheets

(51) Int. Cl.
*F01N 11/00* (2006.01)
*G01N 33/00* (2006.01)
*G01N 15/00* (2006.01)

(52) U.S. Cl.
CPC ...... *G01N 33/0036* (2013.01); *F01N 2560/05* (2013.01); *F01N 2560/12* (2013.01); *G01N 2015/0046* (2013.01); *Y02A 50/25* (2018.01)

(58) Field of Classification Search
USPC ..................................................... 73/28.02
See application file for complete search history.

(56) References Cited

U.S. PATENT DOCUMENTS

2014/0352405 A1   12/2014   Motomura et al.
2015/0102822 A1   4/2015    Okuda

FOREIGN PATENT DOCUMENTS

WO   WO-2012/098290 A   7/2012
WO   WO-2013/175548 A   11/2013

* cited by examiner

PARTICULATE SENSOR

This application claims the benefit of Japanese Patent Application No. 2016-103466, filed May 24, 2016, which is incorporated herein in its entirety by reference.

FIELD OF THE INVENTION

The present invention relates to a particulate sensor.

BACKGROUND OF THE INVENTION

Exhaust gas discharged from an internal combustion engine (for example, a diesel engine) may contain particulates such as soot. Exhaust gas containing such particulates is purified by means of collecting the particulates through use of a filter. Also, if necessary, the filter is heated to high temperature so as to burn and remove particulates having accumulated in the filter. Therefore, if the filter suffers breakage or a like failure, unpurified exhaust gas is discharged directly to the downstream side of the filter. Therefore, there has been demanded a particulate detection sensor that can detect the quantity of particulates contained in exhaust gas in order to directly measure the quantity of particulates contained in exhaust gas or to detect a failure of the filter.

For example, Japanese Patent Application Laid-Open (kokai) No. 2015-129712 discloses such a particulate sensor. The particulate sensor includes a tubular gas introduction pipe extending from the rear end side toward the forward end side in the axial direction of the particulate sensor, and a discharge electrode member which produces ions by means of gaseous discharge. The gas introduction pipe has a gas introduction opening which is located on the rear end side of the gas introduction pipe and through which a gas under measurement (target gas) containing particulates is introduced into the gas introduction pipe, and a gas discharge opening which is located on the forward end side of the gas introduction pipe and through which the gas under measurement is discharged to the outside of the gas introduction pipe. The discharge electrode member is located rearward of the gas discharge opening. This particulate sensor causes the ions produced as a result of gaseous discharge to adhere to the particulates contained in the gas under measurement within the gas introduction pipe, to thereby produce electrified particulates; and detects the particulates contained in the gas under measurement through use of a signal current which flows in accordance with the amount of ions contained in the electrified particulates discharged to the outside of the gas introduction pipe through the gas discharge opening.

Problem to be Solved by the Invention

Incidentally, in the particulate sensor of Japanese Patent Application Laid-Open (kokai) No. 2015-129712, the gas introduction pipe is maintained at a collection potential and is used as a collection electrode for collecting floating ions; i.e., ions that have been generated as a result of gaseous discharge but which have failed to adhere to the particulates. Further, the particulate sensor includes, in addition to the discharge electrode member, an auxiliary electrode member which applies a repulsive force to the floating ions toward the gas introduction pipe to thereby assist the collection of the floating ions by the gas introduction pipe. However, when the auxiliary electrode member is provided, in addition to the auxiliary electrode member, there must be provided a power supply circuit for supplying electric power to the auxiliary electrode member, a cable for connecting the power supply circuit to the auxiliary electrode member, etc. Therefore, the number of constituent elements of the particulate sensor increases, which results in high production cost of the particulate sensor. Also, since electric power to be supplied to the auxiliary electrode member is needed, the amount of electric power used in the particulate sensor increases. In view of these drawbacks, the present inventors have considered removal of the auxiliary electrode member from the particulate sensor.

However, when the auxiliary electrode member is removed from the particulate sensor, the floating ions become more likely to be discharged to the outside of the gas introduction pipe through the gas discharge opening. Specifically, ions that have been produced near the forward end of the discharge electrode member but which have failed to adhere to the particulates tend to flow, as floating ions, toward the gas discharge opening; i.e., toward the forward end side in the axial direction. Therefore, the amount of floating ions which reach the gas discharge opening without hitting against (adhering to) the gas introduction pipe may increase, and the amount of floating ions which cannot be collected by the gas introduction pipe may increase. Namely, there may be increased the amount of floating ions which are discharged, together with electrified particulates, to the outside of the gas introduction pipe through the gas discharge opening.

The above-described particulate sensor detects the particulates contained in the gas under measurement through use of a signal current which flows in accordance with the amount of ions contained in the electrified particulates discharged to the outside of the gas introduction pipe through the gas discharge opening. Therefore, if floating ions are discharged, together with electrified particulates, to the outside of the gas introduction pipe through the gas discharge opening, the signal current flows in accordance with the sum of the amount of the ions contained in the electrified particulates and the amount of the floating ions. Namely, the magnitude of the detected signal current deviates (has an offset) from the magnitude of the signal current flowing in accordance with the amount of ions contained in the electrified particulates discharged to the outside of the gas introduction pipe through the gas discharge opening, by an amount corresponding to the magnitude of the signal current flowing in accordance with the amount of floating ions discharged to the outside of the gas introduction pipe through the gas discharge opening. Accordingly, there is produced a detection error corresponding to the magnitude of the signal current flowing in accordance with the amount of floating ions discharged to the outside of the gas introduction pipe through the gas discharge opening. Therefore, if the auxiliary electrode member is removed from the particulate sensor, there arises a possibility that the amount of floating ions discharged to the outside of the gas introduction pipe through the gas discharge opening increases, and the accuracy of particulate detection decreases.

The present invention has been accomplished in view of such a problem, and its object is to provide a particulate sensor which can reduce the amount of floating ions discharged from the interior of a gas introduction pipe to the outside through a gas discharge opening, without providing an auxiliary electrode member which applies a repulsive force to the floating ions toward the gas introduction pipe to thereby assist the collection of floating ions by the gas introduction pipe.

SUMMARY OF THE INVENTION

Means for Solving the Problem

One mode of the present invention is a particulate sensor comprising a tubular gas introduction pipe extending from a rear end side to a forward end side in an axial direction; and a discharge electrode member which is contained in the gas introduction pipe and produces ions by gaseous discharge, the gas introduction pipe has a gas introduction opening which is located on the rear end side of the gas introduction pipe and through which a target gas containing particulates is introduced into an interior of the gas introduction pipe, and a gas discharge opening which is located on the forward end side of the gas introduction pipe and through which the target gas is discharged to the outside of the gas introduction pipe, the discharge electrode member is located on the rear end side with respect to the gas discharge opening, the gas introduction pipe contains the ions produced by the gaseous discharge, which adhere to the particulates contained in the target gas to generate electrified particulates, the particulate sensor detects the particulates contained in the target gas by using a signal current flowing in accordance with the amount of the ions contained in the electrified particulates, which is discharged to the outside of the gas introduction pipe through the gas discharge opening, the gas introduction pipe is maintained at a collection potential and serves as a collection electrode that collects floating ions which do not adhere to the particulates, and the particulate sensor does not have an auxiliary electrode member which applies to the floating ions a repulsive force toward the gas introduction pipe to thereby assist the collection of the floating ions by the gas introduction pipe, and has a collection member which is connected to the gas introduction pipe to thereby be maintained at the collection potential and is disposed between a forward end of the discharge electrode member and the gas discharge opening such that the forward end of the discharge electrode member cannot be visually recognized from the outside of the gas introduction pipe through the gas discharge opening.

The above-described particulate sensor does not have an auxiliary electrode member which applies to floating ions (ions that have been produced as a result of gaseous discharge but which have failed to adhere to particulates) a repulsive force toward the gas introduction pipe to thereby assist the collection of the floating ions by the gas introduction pipe. Since a power supply circuit for supplying electric power to the auxiliary electrode member, a cable for connecting the power supply circuit to the auxiliary electrode member, etc. can be eliminated as a result of elimination of the auxiliary electrode member, the configuration of the particulate sensor can be simplified, and the production cost of the particulate sensor can be decreased. Also, through elimination of the auxiliary electrode member, the amount of electric power used in the particulate sensor can be decreased.

Further, in the above-described particulate sensor, the auxiliary electrode member is eliminated, and instead, the collection member connected to the gas introduction pipe to thereby be maintained at a collection potential is disposed inside the gas introduction pipe. This collection member is disposed in the gas introduction pipe to be located between the forward end of the discharge electrode member and the gas discharge opening such that the forward end of the discharge electrode member cannot be visually recognized from the outside of the gas introduction pipe through the gas discharge opening. In other words, the collection member is disposed in the gas introduction pipe to be located between the forward end of the discharge electrode member and the gas discharge opening such that all straight lines (line segments) which connect the forward end of the discharge electrode member and the gas discharge opening intersect with the collection member.

Therefore, even when floating ions which are ions that have been produced near the forward end of the discharge electrode member but which have failed to adhere to the particulates cannot be caused to hit against (adhere to) the gas introduction pipe while flowing toward the gas discharge opening, at least a portion of the floating ions can be caused to hit against (adhere to) the collection member and be collected by the collection member.

Accordingly, in the above-described particulate sensor, the amount of the floating ions which are discharged from the interior of the gas introduction pipe to the outside together with the electrified particulates can be reduced without providing an auxiliary electrode member which applies a repulsive force to floating ions toward the gas introduction pipe to thereby assist the collection of the floating ions by the gas introduction pipe. As a result, in the above-described particulate sensor, since the signal current which flows in accordance with the amount of the floating ions discharged from the interior of the gas introduction pipe to the outside can be decreased, the accuracy of particulate detection can be improved.

In the above-described particulate sensor, preferably, the gas discharge opening is open in the axial direction; the forward end of the discharge electrode member is located within a cylindrical region of the gas introduction pipe which is surrounded by an imaginary tube formed by extending a perimeter of the gas discharge opening toward the rear end side in the axial direction; and the collection member is disposed at a position where the collection member intersects with all straight lines extending in the axial direction while passing through the gas discharge opening.

In the above-described particulate sensor, the gas discharge opening is located at the forward end of the gas introduction pipe and is open in the axial direction. Also, the forward end of the discharge electrode member is located within the gas introduction pipe and is also located within a cylindrical region surrounded by an imaginary tube which extends from the perimeter (peripheral edge) of the gas discharge opening toward the rear end side in the axial direction. In such a particulate sensor, at least a portion of the floating ions which are ions that have been produced near the forward end of the discharge electrode member but which have failed to adhere to the particulates flows toward the forward end side in the axial direction; i.e., toward the gas discharge opening.

In contrast, in the above-described particulate sensor, the collection member is disposed at a position where the collection member intersects all the straight lines which extend in the axial direction through the gas discharge opening. Therefore, even when the floating ions which flow toward the forward end side in the axial direction; i.e., toward the gas discharge opening, cannot be caused to hit against (adhere to) the gas introduction pipe for collection thereof, the floating ions can be caused to hit against (adhere to) the collection member and be collected by the collection member. Accordingly, in the above-described particulate sensor, the amount of floating ions discharged from the interior of the gas introduction pipe to the outside can be reduced without providing an auxiliary electrode member.

In the above-described particulate sensor, preferably, the collection member includes a plurality of plate-shaped portions arranged at predetermined intervals in the axial direction such that the plate-shaped portions divide the internal space of the gas introduction pipe; each plate-shaped portion has a through hole which penetrates the plate-shaped portion in the axial direction; and the through holes of the plate-shaped portions located adjacent to each other in the axial direction are formed such that the through hole of one of the plate-shaped portions does not overlap the through hole of the other plate-shaped portion as viewed in the axial direction.

In the above-described particulate sensor, the collection member has a plurality of plate-shaped portions which are arranged at predetermined intervals in the axial direction so as to divide the internal space of the gas introduction pipe. Accordingly, the internal space of the gas introduction pipe is divided into a plurality of the axially arranged internal subspaces by the plurality of plate-shaped portions spaced from one another in the axial direction. Further, each of the plate-shaped portions has a through hole penetrating therethrough in the axial direction.

Accordingly, each plate-shaped portion can guide (cause) the target gas containing electrified particulates and floating ions to flow, through its through hole, from the internal subspace located on the rear end side of that plate-shaped portion to the internal subspace located on the forward end side of that plate-shaped portion. Namely, the target gas containing electrified particulates and ions flows, through the through hole of each plate-shaped portion, from the internal subspace located on the rear end side of that plate-shaped portion to the internal subspace located on the forward end side of that plate-shaped portion.

Further, in the above-described particulate sensor, the through holes of the plate-shaped portions located adjacent to each other in the axial direction are formed at positions determined such that the through hole of one of the plate-shaped portions does not overlap with the through hole of the other of the plate-shaped portions as viewed in the axial direction. Since the collection member has such a structure, for example, when floating ions flow, through the through hole of a plate-shaped portion located closest to the rear end side in the axial direction, from the internal subspace located on the rear end side of that plate-shaped portion to the internal subspace located on the forward end side of that plate-shaped portion, a plate-shaped portion (a portion thereof where the through hole is not formed) adjacently located on the forward end side of the rearmost plate-shaped portion is present in a region to which the floating ions flow (i.e., in a direction in which the floating ions advance). Therefore, the floating ions having passed through the through hole of the rearmost plate-shaped portion become more likely to hit against (adhere to) the plate-shaped portion adjacently located on the forward end side of the rearmost plate-shaped portion. The same is true of the remaining plate-shaped portions located adjacent to one another in the axial direction.

As described above, in the above-described particulate sensor, the collection member is configured such that the target gas containing electrified particulates and floating ions can flow from the rear end side toward the forward end side of the collection member through the through holes of the plate-shaped portions of the collection member, and the floating ions are more likely to be collected by the collection member. Namely, the likelihood of collection of floating ions by the collection member is increased by constituting the collection member by a plurality of plate-shaped portions having through holes which satisfy the above-described positional relation. Accordingly, the above-described particulate sensor can further decrease the amount of floating ions discharged from the interior of the gas introduction pipe to the outside without providing an auxiliary electrode member.

In the above-described particulate sensor, preferably, the particulate sensor is attached to a metallic gas flow pipe through which the target gas flows and which is maintained at a ground potential; the gas introduction pipe is maintained at the collection potential different from the ground potential; the discharge electrode member is maintained at a discharge potential different from the ground potential and the collection potential and generates the gaseous discharge between the discharge electrode member and the gas introduction pipe; the gas discharge opening is disposed within the gas flow pipe; and the particulate sensor detects the amount of the particulates contained in the target gas by using the signal current flowing between the collection potential and the ground potential in proportion to the amount of the ions discharged from the interior of the gas introduction pipe into the gas flow pipe through the gas discharge opening.

The above-described particulate sensor is attached to a gas flow pipe through which the target gas flows and which is formed of metal and is maintained at a ground potential (a potential different from the collection potential) and is used in such a state. The discharge electrode member is maintained at a discharge potential different from the ground potential and the collection potential, and generates gaseous discharge between the discharge electrode member and the gas introduction pipe. The gas discharge opening of the gas introduction pipe is disposed within the gas flow pipe. In such a particulate sensor, the amount of particulates contained in the target gas is detected through use of a signal current which flows between the collection potential and the ground potential in accordance with the amount of ions discharged from the interior of the gas introduction pipe into the gas flow pipe through the gas discharge opening.

In such a particulate sensor as well, as described above, the amount of floating ions discharged from the interior of the gas introduction pipe to the outside (into the gas flow pipe) can be reduced without providing an auxiliary electrode. Therefore, the signal current flowing in accordance with the amount of the floating ions can be decreased. As a result, the magnitude of the detected signal current (the measurement value of the signal current) can be rendered closer to the magnitude of the signal current which flows in accordance with the amount of ions contained in the electrified particulates discharged to the outside of the gas introduction pipe through the gas discharge opening, whereby the accuracy of particulate detection can be improved.

BRIEF DESCRIPTION OF THE DRAWINGS

These and other features and advantages of the present invention will become more readily appreciated when considered in connection with the following detailed description and appended drawings, wherein like designations denote like elements in the various views, and wherein.

DETAILED DESCRIPTION OF THE INVENTION

Modes for Carrying Out the Invention

Embodiment

Figure 1:
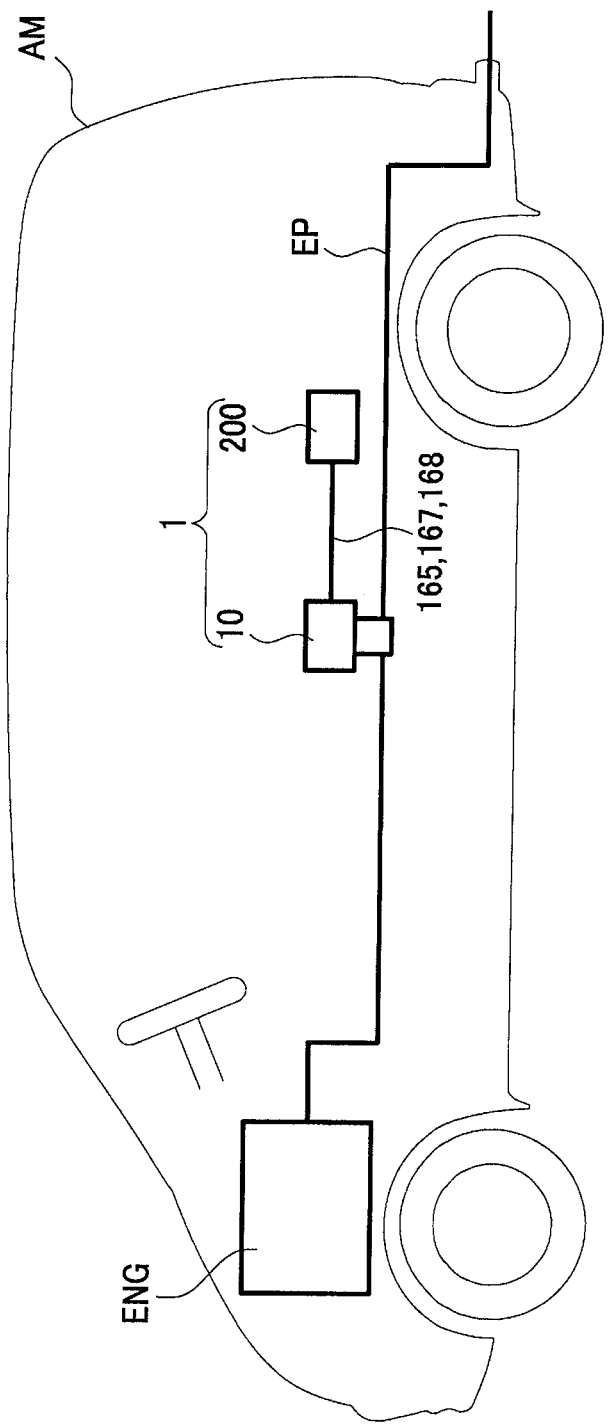
FIG. 1 is a schematic view of a vehicle on which a particulate detection system according to an embodiment is mounted.
Figure 2:
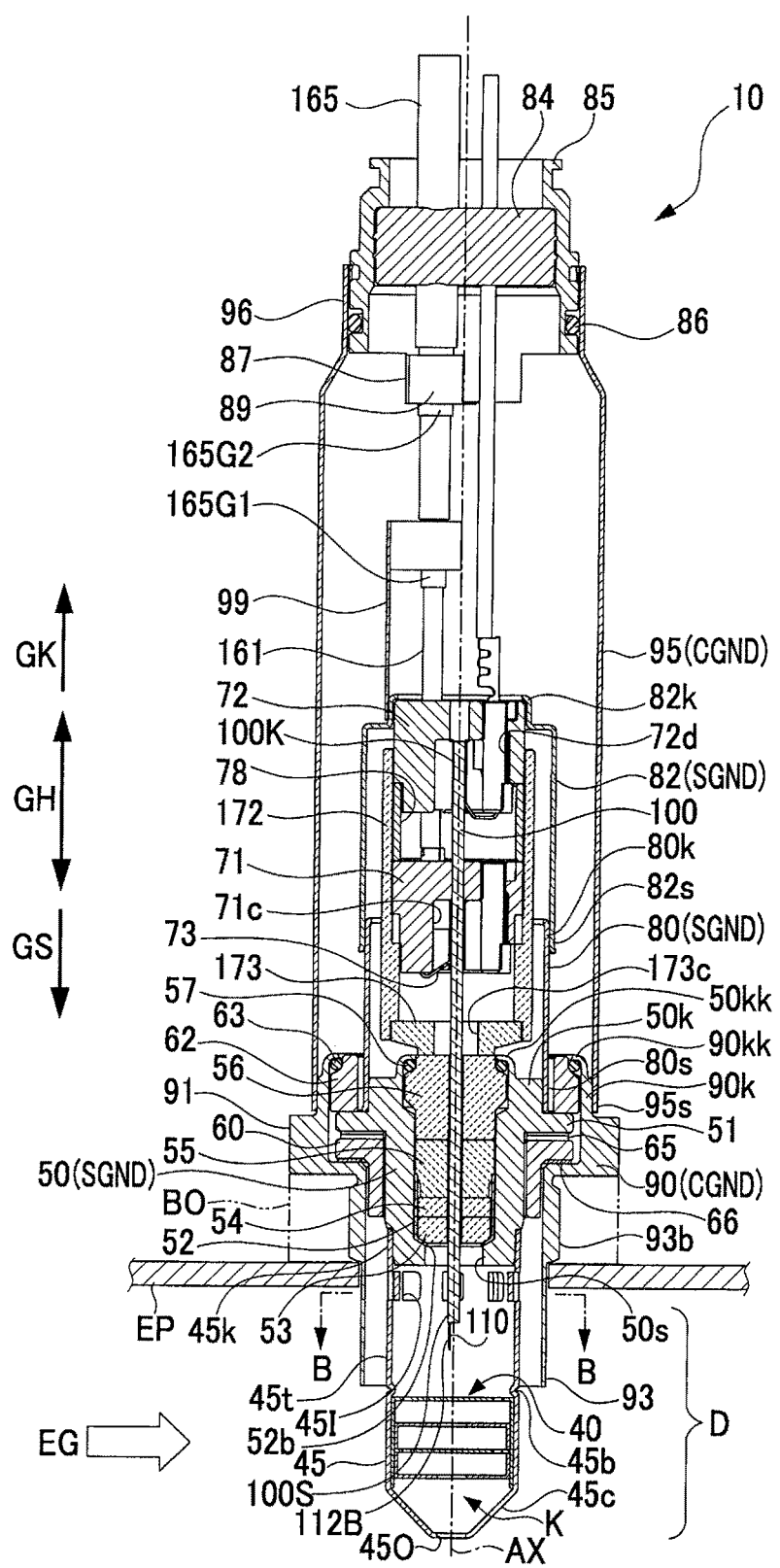
FIG. 2 is a longitudinal sectional view of a particulate sensor according to the embodiment.
Figure 3:
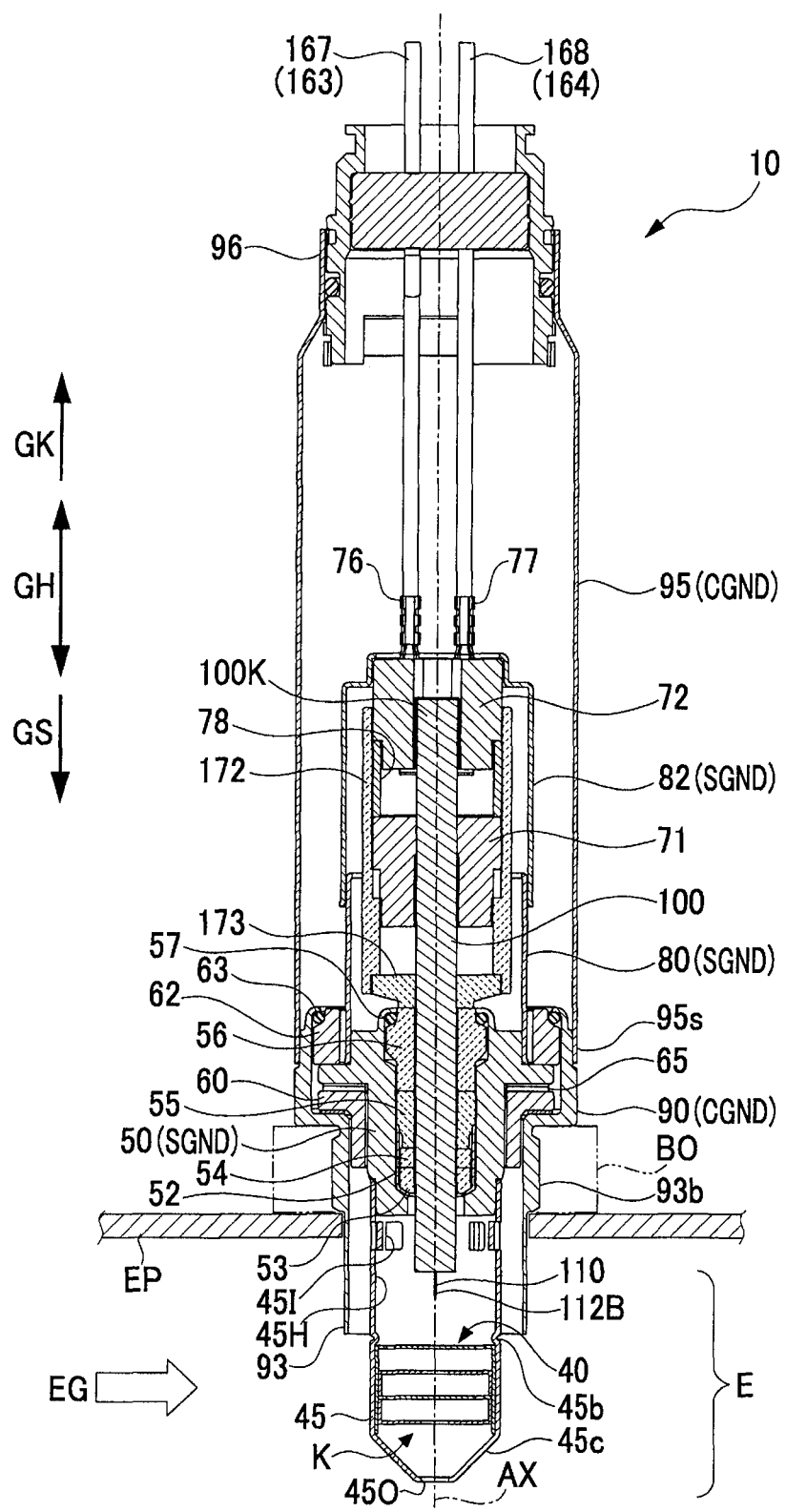
FIG. 3 is another longitudinal sectional view of the particulate sensor.
Figure 4:
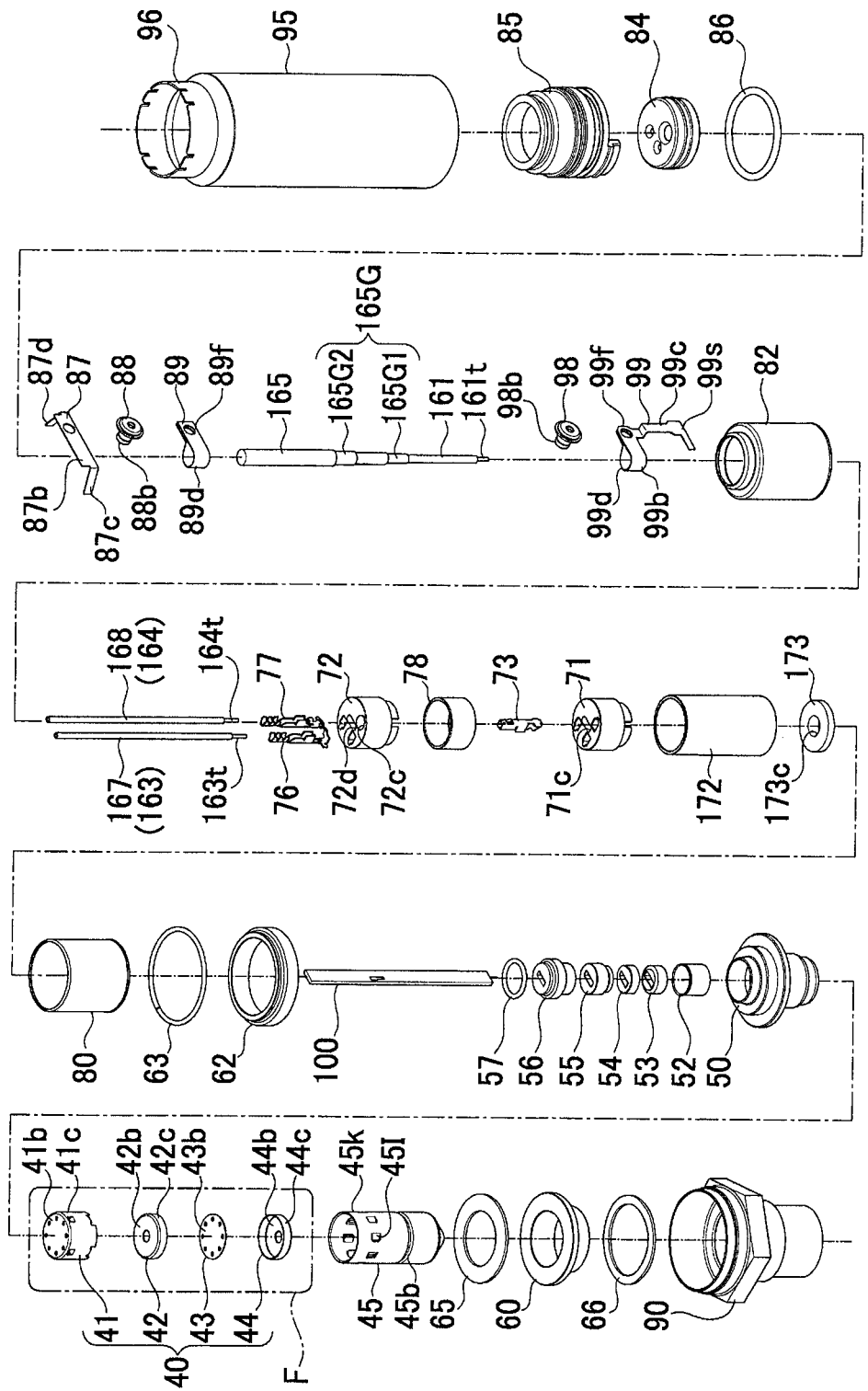
FIG. 4 is an exploded perspective view of the particulate sensor.
Figure 5:
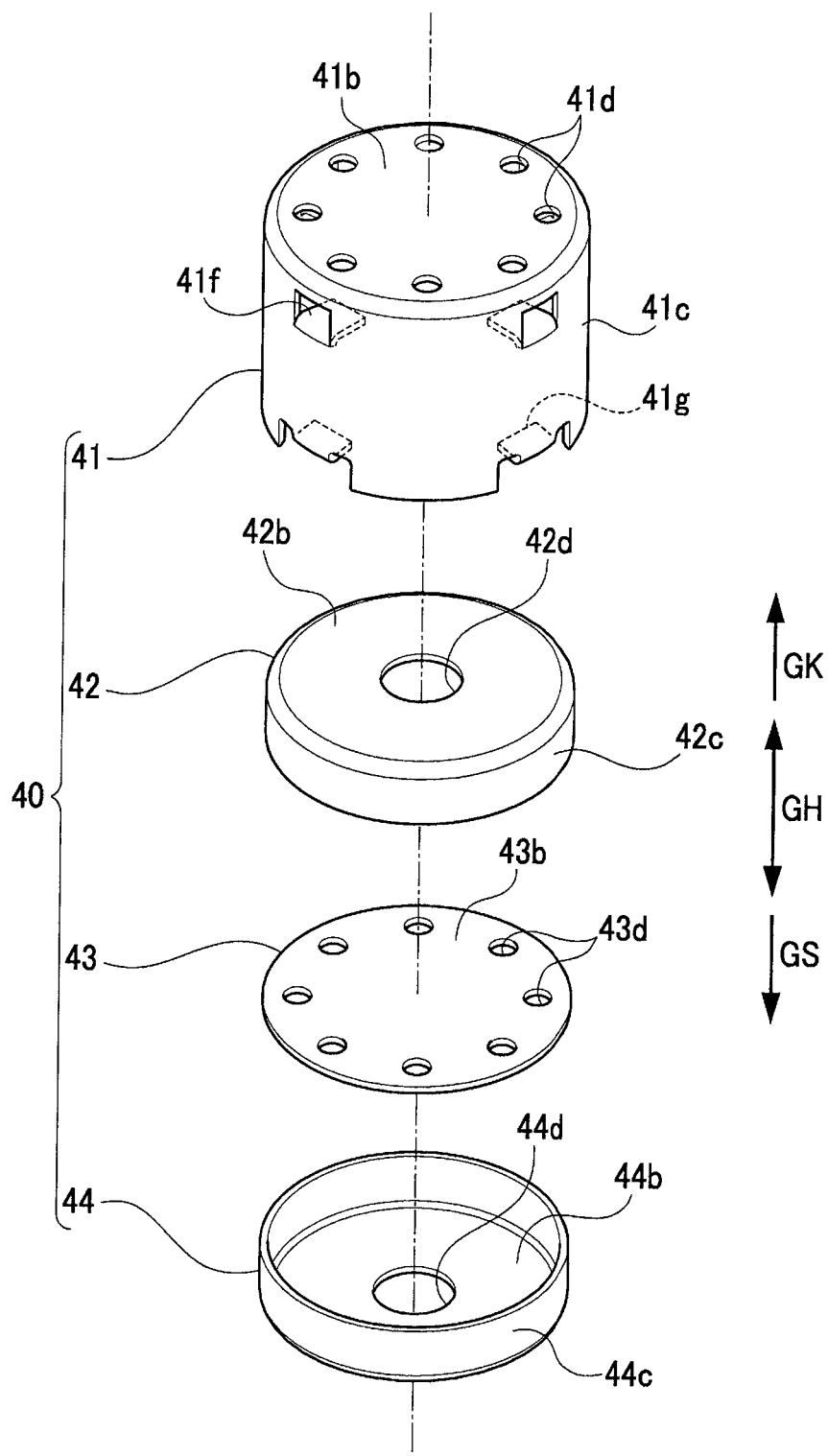
FIG. 5 is an enlarged view of portion F of FIG. 4.
Figure 6:
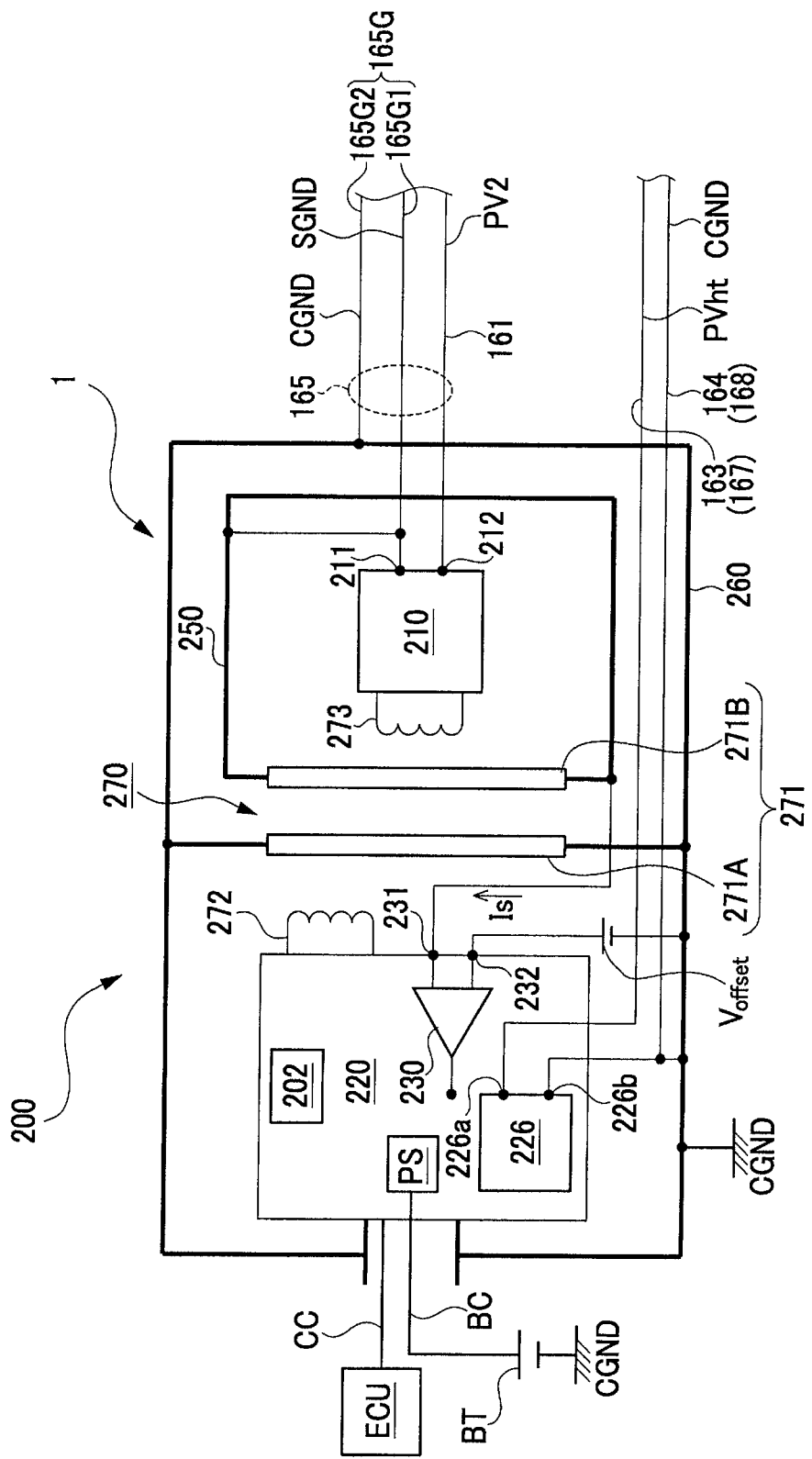
FIG. 6 is a schematic diagram of the particulate detection system.

An embodiment of the present invention will be described with reference to the drawings. FIG. 1 is a schematic view of a vehicle AM on which a particulate detection system 1 according to the embodiment is mounted. FIG. 2 is a longitudinal sectional view of a particulate sensor 10 according to the embodiment. FIG. 3 is another longitudinal sectional view of the particulate sensor 10, which is obtained by cutting the sensor at a position shifted 90° from the cut position of FIG. 2 about an axial line AX. FIG. 4 is an exploded perspective view of the particulate sensor 10. FIG. 5 is an enlarged view of portion F of FIG. 4. FIG. 6 is a schematic diagram of the particulate detection system 1. However, in FIG. 6, a control apparatus 200 contained in the particulate detection system 1 is mainly shown, and only a portion (an electric wire 165, etc.) of the particulate sensor 10 is shown.

As shown in FIG. 2, with respect to the axial direction GH of the particulate sensor 10 (the direction in which the axial line AX extends, the vertical direction in FIG. 2), the side where a protector 45 (a gas introduction pipe) is disposed (the lower side in FIG. 2) will be referred as the forward end side GS, and the opposite side where the electric wire 165, etc. extend outward (the upper side in FIG. 2) will be referred as the rear end side GK.

As shown in FIG. 1, the particulate detection system 1 (hereinafter also referred to as the "system 1" for simplicity) includes the particulate sensor 10 and the control apparatus 200 for controlling the particulate sensor 10. The particulate sensor 10 is attached to an exhaust pipe EP (gas flow pipe) of an engine ENG (internal combustion engine) mounted on the vehicle AM, and detects particulates S (soot, etc.) contained in exhaust gas EG (gas under measurement) flowing through the exhaust pipe EP. Specifically, the particulate sensor 10 is fixed to the exhaust pipe EP formed of metal, and a portion of the particulate sensor 10 on the forward end side is disposed in the exhaust pipe EP and is exposed to the exhaust gas EG (see FIG. 2)

The control apparatus 200 is connected to the particulate sensor 10 through the electric wires 165, 167, and 168 (see FIGS. 1 and 6). Of the electric wires 165, 167, and 168, the electric wire 165 is a tri-axial cable, and the electric wires 167 and 168 are thin single core insulated electric wires. Of these electric wires, the electric wire 165 includes a discharge potential lead wire 161 as a core (center conductor) (see FIGS. 4 and 6). Also, the electric wire 167 includes a first heater lead wire 163 as a core, and the electric wire 168 includes a second heater lead wire 164 as a core (see FIGS. 4 and 6).

As shown in FIG. 6, the control apparatus 200 includes an ion source power supply circuit 210 and a measurement control circuit 220. The ion source power supply circuit 210 has a first output terminal 211 maintained at a sensor GND potential SGND and a second output terminal 212 maintained at a discharge potential PV2. The second output terminal 212 is connected to the discharge potential lead wire 161. The discharge potential PV2 is set to a positive high potential (for example, 1 to 2 kV), with respect to the sensor GND potential SGND (reference). Notably, the ion source power supply circuit 210 constitutes a constant-current power supply whose output current is feedback-controlled such that the output current (effective value) is autonomously maintained at a predetermined current value (for example, 5 µA). The ion source power supply circuit 210 outputs a discharge potential PV2 to be applied to a discharge electrode member 110 which will be described later.

The measurement control circuit 220 includes a signal current detection circuit 230 and a heater energization circuit 226. The signal current detection circuit 230 has a first input terminal 231 maintained at the sensor GND potential SGND and a second input terminal 232. The signal current detection circuit 230 detects a signal current Is flowing between the first input terminal 231 and the second input terminal 232. Notably, the sensor GND potential SGND is higher than a chassis GND potential CGND (ground potential) by an offset voltage $V_{offset}$ (specifically, 0.5 V). Accordingly, the second input terminal 232 is maintained at a potential higher than the chassis GND potential CGND by the offset voltage $V_{offset}$ (specifically, 0.5 V).

The heater energization circuit 226 is a circuit for supplying electricity to a heater portion 130 of a sensor element 100, which will be described later, through PWM control. The heater energization circuit 226 has a first heater energization terminal 226a connected to the first heater lead wire 163 and a second heater energization terminal 226b connected to the second heater lead wire 164. Notably, the second heater energization terminal 226b and the second heater lead wire 164 electrically communicate with the chassis GND potential CGND and are maintained at the chassis GND potential CGND. The first heater energization terminal 226a and the first heater lead wire 163 are maintained at a first heater potential PVht with respect to the chassis GND potential CGND (reference).

The ion source power supply circuit 210 is surrounded by an inner circuit case 250 maintained at the sensor GND potential SGND. The first output terminal 211 of the ion source power supply circuit 210 and the first input terminal 231 of the signal current detection circuit 230 are connected to the inner circuit case 250.

Notably, in the present embodiment, the inner circuit case 250 accommodates and surrounds the ion source power supply circuit 210 and a secondary-side core 271B of an isolation transformer 270, and electrically communicates with the first output terminal 211 of the ion source power supply circuit 210, whereby the inner circuit case 250 is maintained at the sensor GND potential SGND. The first output terminal 211 of the ion source power supply circuit 210 electrically communicates with an inner external conductor 165G1 of a coaxial double external conductor 165G of the electric wire 165, the inner external conductor 165G1 being maintained at the sensor GND potential SGND.

The core 271 of the isolation transformer 270 is divided into a primary-side core 271A around which a primary-side coil 272 is wound and a secondary-side core 271B around which a power-supply-circuit-side coil 273 is wound. The primary-side core 271A electrically communicates with the chassis GND potential CGND. Meanwhile, the secondary-side core 271B electrically communicates with the sensor GND potential SGND (the first output terminal 211 of the ion source power supply circuit 210).

The ion source power supply circuit 210, the inner circuit case 250, and the measurement control circuit 220 including the signal current detection circuit 230 and the heater energization circuit 226 are surrounded by an outer circuit case 260 maintained at the chassis GND potential CGND. Further, the second input terminal 232 of the signal current detection circuit 230, the second heater energization terminal 226b of the heater energization circuit 226, and the primary-side core 271A of the isolation transformer 270 are connected to the outer circuit case 260 and are maintained at the chassis GND potential CGND.

Notably, in the present embodiment, the outer circuit case 260 accommodates and surrounds the ion source power supply circuit 210, the inner circuit case 250, the measurement control circuit 220 including the signal current detection circuit 230 and the heater energization circuit 226, and the primary-side core 271A of the isolation transformer 270. Further, the outer circuit case 260 electrically communicates with an outer external conductor 165G2 of the coaxial double external conductor 165G of the electric wire 165, the outer external conductor 165G2 being maintained at the chassis GND potential CGND.

The measurement control circuit 220 includes a regulator power supply PS. This regulator power supply PS is connected, through a power supply cable BC, to an external battery BT mounted on the vehicle AM, and is driven by the battery BT. Also, the GND potential of the battery BT is made common with the chassis GND potential CGND. Also, the measurement control circuit 220 includes a microprocessor 202, and can communicate, through a communication line CC, with a control unit ECU which controls the internal combustion engine ENG. Thus, the measurement control circuit 220 can transmit to the control unit ECU a signal representing, for example, the measurement result (the magnitude of the signal current Is) of the above-described signal current detection circuit 230.

A portion of the electric power externally supplied to the measurement control circuit 220 through the regulator power supply PS is distributed to the ion source power supply circuit 210 through the isolation transformer 270. Notably, in the isolation transformer 270, the primary-side coil 272, which partially constitutes the measurement control circuit 220, the power-supply-circuit-side coil 273, which partially constitutes the ion source power supply circuit 210, and the core 271 (the primary-side core 271A and the secondary-side core 271B) are electrically insulated from one another. Therefore, it is possible to distribute electric power from the measurement control circuit 220 to the ion source power supply circuit 210, while maintaining the electrical insulation among them.

Next, the particulate sensor 10 will be described with reference to FIGS. 2 to 4.

As shown in FIGS. 2 and 3, the particulate sensor 10 extends from the rear end side (the upper side in FIG. 2) toward the forward end side (the lower side in FIG. 2) in the axial direction GH (the direction in which the axial line AX extends, the vertical direction in FIG. 2). The particulate sensor 10 includes a sensor element 100 which generates ions CP by means of gaseous discharge (specifically, corona discharge). The sensor element 100 has the shape of a plate extending in the axial direction GH. In addition to that, the particulate sensor 10 includes a metallic shell 50 which holds the sensor element 100, while being electrically isolated from the sensor element 100, and which is maintained at the sensor GND potential SGND. Also, the particulate sensor 10 includes a mounting metallic member 90 which surrounds and holds the metallic shell 50, while being electrically isolated from the metallic shell 50, and which is attached to the exhaust pipe EP to thereby be maintained at the chassis GND potential CGND.

More specifically, the particulate sensor 10 has the tubular mounting metallic member 90 provided on the forward end side GS thereof. The mounting metallic member 90 has a flange portion 91 which bulges radially outward so as to form a hexagonal outer shape. Further, the mounting metallic member 90 has a tubular wall portion 93 which is located on the forward end side GS of the flange portion 91 and which surrounds the outer circumference of a protector 45 (the gas introduction pipe) which will be described later. A male screw 93b used to fix the particulate sensor 10 to the exhaust pipe EP is formed on the outer circumference of a portion of the tubular wall portion 93 on the rear end side GK. Accordingly, through use of the male screw 93b of the mounting metallic member 90, the particulate sensor 10 is attached to an attachment boss BO which is formed of metal and is separately fixed to the exhaust pipe EP, whereby the particulate sensor 10 is fixed to the exhaust pipe EP via the attachment boss BO. Therefore, the mounting metallic member 90 is maintained at the chassis GND potential CGND, which is the same as the potential of the exhaust pipe EP.

Also, an outer tube 95 formed of metal is fixed to an end of the mounting metallic member 90 on the rear end side GK. Specifically, a forward end portion 95s of the outer tube 95 is fitted onto a rear end portion 90k of the mounting metallic member 90, and the rear end portion 90k of the mounting metallic member 90 and the forward end portion 95s of the outer tube 95 are laser-welded together, whereby the mounting metallic member 90 and the outer tube 95 are integrated.

The tubular metallic shell 50 and an inner tube 80 integrated therewith are disposed on the radially inner side of the mounting metallic member 90, with an insulating spacer 60 formed of an electrically insulating material being interposed therebetween. Also, together with these members, a tubular sleeve 62 and an annular line packing 63 are disposed within the mounting metallic member 90.

Specifically, the metallic shell 50 has a generally cylindrical shape and has an annular flange 51 bulging radially outward. The inner tube 80 is formed of metal and has the shape of a cylindrical tube extending in the axial direction GH. A forward end portion 80s of the inner tube 80 is fitted onto a rear end portion 50k of the metallic shell 50 so that the forward end of the inner tube 80 butts against the flange 51 of the metallic shell 50. The rear end portion 50k of the metallic shell 50 and the forward end portion 80s of the inner tube 80 are laser-welded together, whereby the metallic shell 50 and the inner tube 80 are integrated.

The flange 51 of the metallic shell 50 is disposed within the mounting metallic member 90 in such a manner that the flange 51 is sandwiched between the insulating spacer 60 located on the forward end side GS and the sleeve 62 located on the rear end side GK. Notably, an annular packing 65 formed of carbon graphite is interposed between the flange 51 of the metallic shell 50 and the insulating spacer 60 so as to secure the gas tightness between the flange 51 of the metallic shell 50 and the insulating spacer 60. Also, an annular packing 66 formed of carbon graphite is interposed between the insulating spacer 60 and the mounting metallic member 90 so as to secure the gas tightness between the insulating spacer 60 and the mounting metallic member 90. The line packing 63 is disposed between the sleeve 62 and a rearmost end portion 90kk of the mounting metallic member 90, and the rearmost end portion 90kk of the mounting metallic member 90 is bent radially inward by means of crimping.

A metal cup 52 is disposed within the metallic shell 50. The metal cup 52 has a hole 52b formed in the bottom wall thereof, and the sensor element 100 extends through the hole 52b. Around the sensor element 100, a tubular ceramic holder 53 formed of alumina and holding the sensor element 100, first and second powder charged layers 54 and 55 formed by compressing powder of talc, and a tubular ceramic sleeve 56 formed of alumina are disposed in this order from the forward end side GS toward the rear end side GK. Of these, the ceramic holder 53 and the first powder charged layer 54 are located within the metal cup 52.

Further, a crimp ring 57 is disposed between the rearmost end portion 50kk of the metallic shell 50 and the ceramic sleeve 56. The rearmost end portion 50kk of the metallic shell 50 is bent radially inward by means of crimping, to thereby press the ceramic sleeve 56 through the crimp ring 57. As a result, the powder of the second powder charged layer 55 is compressed, whereby the metal cup 52 and the ceramic sleeve 56 are fixed within the metallic shell 50, and the sensor element 100 is gastightly held by the metallic shell 50.

The tubular protector 45 (the gas introduction pipe) formed of stainless steel is fixedly provided at a forward end portion 50s of the metallic shell 50, and surrounds a forward end portion 100S of the sensor element 100 from the radially outer side. The protector 45 protects the sensor element 100 from water droplets and foreign substances, and introduces the exhaust gas EG into a space around the forward end portion 100S of the sensor element 100. The protector 45 is fixed to the forward end portion 50s of the metallic shell 50 as follows. Specifically, a rear end portion 45k of the protector 45 is fitted onto the forward end portion 50s of the metallic shell 50, and the forward end portion 50s of the metallic shell 50 and the rear end portion 45k of the protector 45 are laser-welded together, whereby the protector 45 is fixed to the forward end portion 50s of the metallic shell 50. A portion of the protector 45 on the forward end side GS is a taper portion 45c tapered such that its diameter decreases toward the forward end side GS.

A plurality of gas introduction holes 45I are formed in a portion of the protector 45 on the rear end side GK at equal intervals in the circumferential direction (see FIGS. 2 and 4). The exhaust gas EG (gas under measurement) containing the particulates S is introduced into the interior of the protector 45 through the gas introduction holes 45I. Further, a gas discharge opening 45O for discharging the introduced exhaust gas EG (gas under measurement) is formed in a forward end portion of the protector 45. The gas discharge opening 45O is a single circular opening whose axis coincides with the axial line AX of the particulate sensor 10 and which is provided at the forward end of the protector 45.

Notably, a rear tubular portion 45t of the protector 45 where the gas introduction openings 45I are formed is circumferentially surrounded by the tubular wall portion 93 of the mounting metallic member 90 with an annular gap formed therebetween. As a result, the gas introduction openings 45I are covered from the outer side by the tubular wall portion 93.

A collection member 40 is disposed in the interior (internal space K) of the protector 45 to be located between the forward end 110s of the discharge electrode member 110 and the gas discharge opening 45O. As will be described later, this collection member 40 is connected to the protector 45 (the gas introduction pipe) and is maintained at a collection potential (equal to the sensor GND potential SGND in the present embodiment), and collects floating ions CPF in cooperation with the protector 45 (see FIG. 9).

The collection member 40 is composed of a first collection portion 41, a second collection portion 42, a third collection portion 43, and a fourth collection portion 44 (see FIGS. 4 and 5). The first collection portion 41 is composed of a plate-shaped portion 41b having a disk-like shape, and a cylindrical support portion 41c extending from the plate-shaped portion 41b toward the forward end side GS (see FIG. 5). A plurality of through holes 41d are formed in a peripheral edge portion of the plate-shaped portion 41b such that they penetrate the plate-shaped portion 41b in the axial direction GH. Notably, the through holes 41d are formed at eight locations which are equally spaced from one another in the circumferential direction of the peripheral edge portion of the plate-shaped portion 41b.

A plurality of rear-end-side bent portions 41f and a plurality of forward-end-side bent portions 41g are formed in the support portion 41c of the first collection portion 41 (see FIG. 5). The rear-end-side bent portions 41f are formed by forming, by means of cutting, rectangular tabs in a portion on the rear end side GK of the side wall of the support portion 41c, and bending the rectangular tabs radially inward. The rear-end-side bent portions 41f extend from the side wall of the support portion 41c toward the radially inner side. The forward-end-side bent portions 41g are formed by forming, by means of cutting, rectangular tabs in a forward end portion of the side wall of the support portion 41c, and bending the rectangular tabs radially inward. The forward-end-side bent portions 41g extend from the side wall of the support portion 41c toward the radially inner side. Notably, the rear-end-side bent portions 41f are provided at four locations which are equally spaced from one another in the circumferential direction of the side wall of the support portion 41c. Similarly, the forward-end-side bent portions 41g are provided at four locations which are equally spaced from one another in the circumferential direction of the side wall of the support portion 41c.

The second collection portion 42 is composed of a plate-shaped portion 42b having a disk-like shape, and a cylindrical support portion 42c extending from the plate-shaped portion 42b toward the forward end side GS. A single cylindrical through hole 42d is formed at the center of the plate-shaped portion 42b such that the through hole 42d penetrates the plate-shaped portion 42b in the axial direction GH. Notably, the axial line of the through hole 42d coincides with the axial line AX of the particulate sensor 10.

The third collection portion 43 has a plate-shaped portion 43b having a disk-like shape. A plurality of through holes 43d are formed in a peripheral edge portion of the plate-shaped portion 43b such that they penetrate the plate-shaped portion 43b in the axial direction GH. Notably, the through holes 43d are formed at eight locations which are equally spaced from one another in the circumferential direction of the peripheral edge portion of the plate-shaped portion 43b.

The fourth collection portion 44 is composed of a plate-shaped portion 44b having a disk-like shape, and a cylindrical support portion 44c extending from the plate-shaped portion 44b toward the rearward end side GK. A single cylindrical through hole 44d is formed at the center of the plate-shaped portion 44b such that the through hole 44d penetrates the plate-shaped portion 44b in the axial direction GH. Notably, the axial line of the through hole 44d coincides with the axial line AX of the particulate sensor 10.

The collection member 40 is formed by integrally combining the first collection portion 41, the second collection portion 42, the third collection portion 43, and the fourth collection portion 44. Specifically, the first collection portion 41 on which the rear-end-side bent portions 41f have been formed without formation of the forward-end-side bent portions 41g thereon is first prepared as the first collection portion 41. Subsequently, the second collection portion 42, the third collection portion 43, and the fourth collection portion 44 are inserted into the interior of the first collection portion 41 from the forward end side GS of the first collection portion 41.

Figure 10:
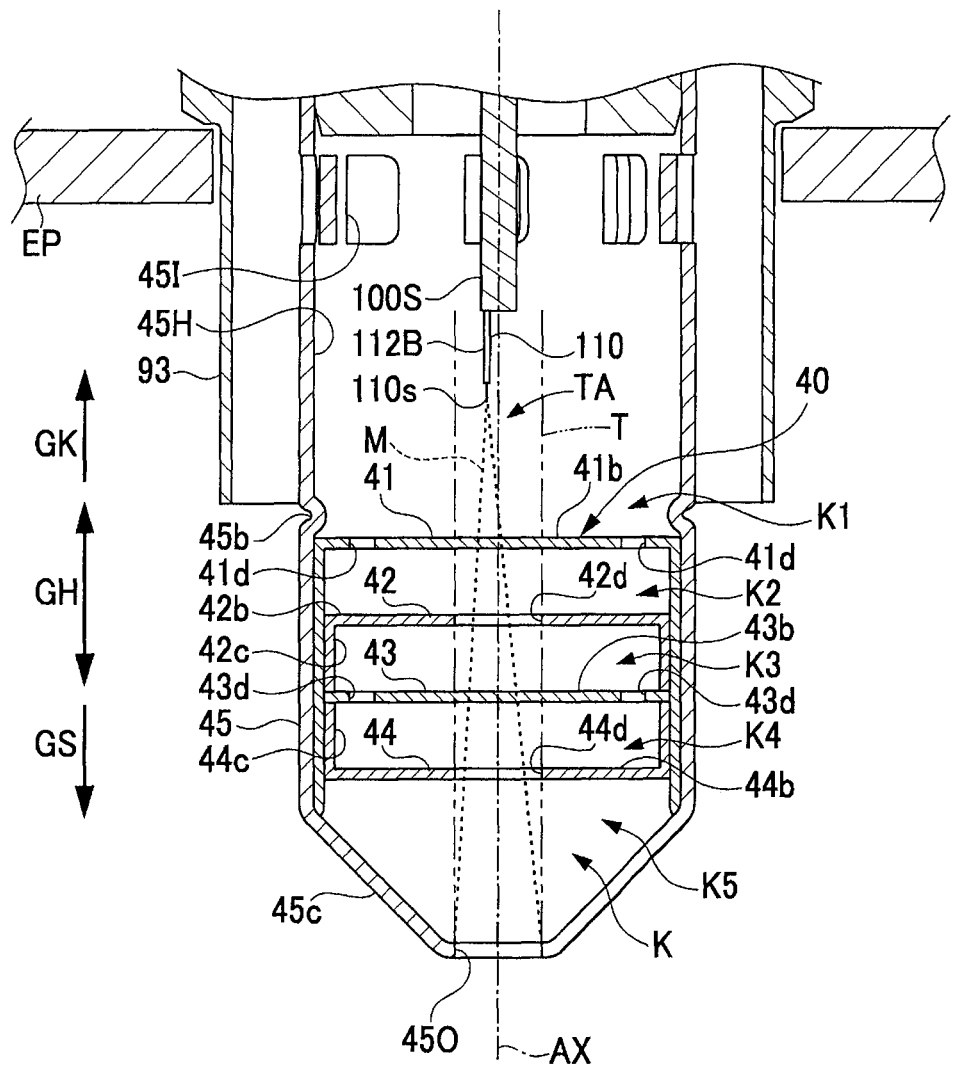
FIG. 10 is an enlarged view of portion D of FIG. 2.
Figure 11:
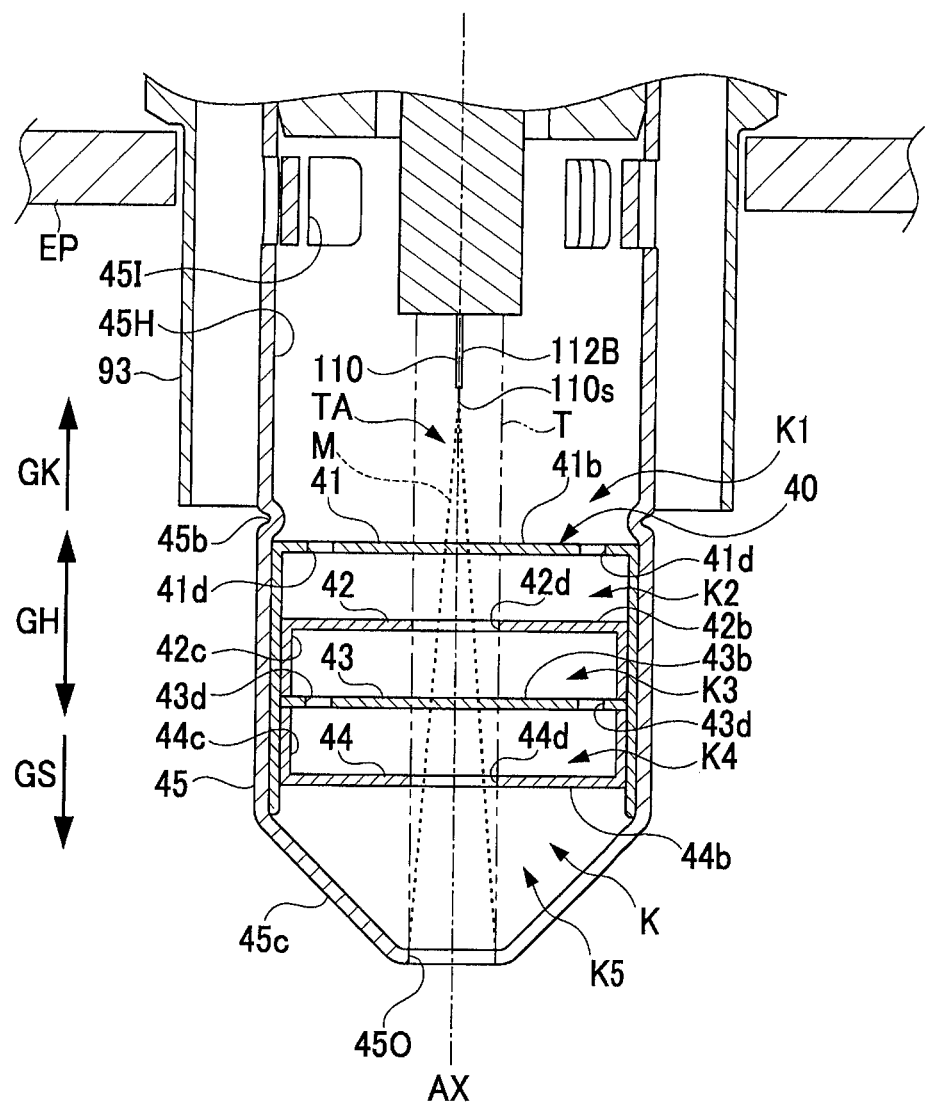
FIG. 11 is an enlarged view of portion E of FIG. 3.

At that time, the plate-shaped portion 42b of the second collection portion 42 butts against the rear-end-side bent portions 41f of the first collection portion 41, so that the plate-shaped portion 41b of the first collection portion 41 and the plate-shaped portion 42b of the second collection portion 42 are arranged side by side in the axial direction GH with a gap formed therebetween (see FIGS. 10 and 11). Further, the plate-shaped portion 43b of the third collection portion 43 butts against the forward end of the support portion 42c of the second collection portion 42, so that the plate-shaped portion 42b of the second collection portion 42 and the plate-shaped portion 43b of the third collection portion 43 are arranged side by side in the axial direction GH with a gap formed therebetween (see FIGS. 10 and 11). Further, the support portion 44c of the fourth collection portion 44 butts against the plate-shaped portion 43b of the third collection portion 43, so that the plate-shaped portion 43b of the third collection portion 43 and the plate-shaped portion 44b of the fourth collection portion 44 are arranged side by side in the axial direction GH with a gap formed therebetween (see FIGS. 10 and 11).

In this state, the forward-end-side bent portions 41g of the first collection portion 41 are formed. As a result, the second collection portion 42, the third collection portion 43, and the fourth collection portion 44 are fixed inside the first collection portion 41 in a state in which they are sandwiched between the rear-end-side bent portions 41f and the forward-end-side bent portions 41g of the first collection portion 41. As a result, the first collection portion 41, the second collection portion 42, the third collection portion 43, and the fourth collection portion 44 are integrally combined, whereby the collection member 40 is completed.

The collection member 40 is fixedly disposed inside the protector 45 (the gas introduction pipe) as follows. Specifically, first, the collection member 40 is press-fitted into the protector 45 from the rear end side GK of the protector 45 (the gas introduction pipe), and the forward end of the support portion 41c of the first collection portion 41 is brought into contact with the taper portion 45c of the protector 45. In this state, an annular portion of the protector 45, which annular portion is located on the rear end side GK of and adjacent to the rear end of the collection member 40 (i.e., the plate-shaped portion 41b of the first collection portion 41), is deformed toward the radially inner side to thereby form an annular recess portion 45b. As a result, the collection member 40 is sandwiched between the annular recess portion 45b and the taper portion 45c of the protector 45, whereby the collection member 40 is fixed inside the protector 45.

In the collection member 40 fixedly disposed inside the protector 45, the plate-shaped portions 41b, 42b, 43b, and 44b are arranged at predetermined intervals in the axial direction GH so as to divide the internal space K of the protector 45 (the gas introduction pipe) in the axial direction GH (see FIGS. 10 and 11). Accordingly, the internal space K of the protector 45 (the gas introduction pipe) is divided into a plurality of internal subspaces K1, K2, K3, K4, and K5 arranged in the axial direction GH by the plate-shaped portions 41b, 42b, 43b, and 44b spaced from one another in the axial direction GH.

The respective through holes of the plate-shaped portions located adjacent to each other in the axial direction GH do not overlap each other in the axial direction GH (see FIGS. 10 and 11). Specifically, as viewed in the axial direction GH, the through holes 41d of the plate-shaped portion 41b do not overlap the through hole 42d of the plate-shaped portion 42b which is located adjacent to the plate-shaped portion 41b in the axial direction GH. Similarly, as viewed in the axial direction GH, the through hole 42d of the plate-shaped portion 42b does not overlap the through holes 43d of the plate-shaped portion 43b which is located adjacent to the plate-shaped portion 42b in the axial direction GH. Similarly, as viewed in the axial direction GH, the through holes 43d of the plate-shaped portion 43b do not overlap the through hole 44d of the plate-shaped portion 44b which is located adjacent to the plate-shaped portion 43b in the axial direction GH.

Here, with reference to FIG. 9, there will be described the introduction and discharge of the exhaust gas EG into and from the interior of the protector 45 at the time when the particulate sensor 10 is used. Notably, in FIG. 9, the exhaust gas EG flows within the exhaust pipe EP from the left-hand side toward the right-hand side. When the exhaust gas EG flowing within the exhaust pipe EP passes through a region around the taper portion 45c of the protector 45 of the particulate sensor 10, its flow speed increases outside the gas discharge opening 45O of the protector 45, and a negative pressure is produced near the gas discharge opening 45O due to the so-called Venturi effect.

By this negative pressure, the introduced exhaust gas EGI introduced into the protector 45 is discharged through the gas discharge opening 45O. Simultaneously, the exhaust gas EG around a forward tubular portion 45m of the protector 45 is introduced into the space between the tubular wall portion 93 of the mounting metallic member 90 and the rear tubular portion 45t of the protector 45, and is then introduced into the interior of the protector 45 through the gas introduction openings 45I of the protector 45. Subsequently, the introduced exhaust gas EGI within the protector 45 is discharged to the outside of the protector 45 through the gas discharge opening 45O. Therefore, within the protector 45, there is produced a flow of the introduced exhaust gas EGI from the gas introduction openings 45I on the rear end side GK toward the gas discharge opening 45O on the forward end side GS.

Notably, the collection member 40 is disposed inside the protector 45. Each of the plate-shaped portions 41b, 42b, 43b, and 44b of the collection member 40 can guide (cause) the exhaust gas EG to flow, through its through hole 41d, 42d, 43d, or 44d, from the internal subspace (K1, K2, K3, or K4) located on the rear end side GK of that plate-shaped portion (41*b*, 42*b*, 43*b*, or 44*b*) to the internal subspace (K2, K3, K4, or K5) located on the forward end side GS of that plate-shaped portion (41*b*, 42*b*, 43*b*, or 44*b*). Accordingly, the introduced exhaust gas EGI flows within the collection member 40 while passing through the through holes 41*d*, 42*d*, 43*d*, and 44*d* of the plate-shaped portions 41*b*, 42*b*, 43*b*, and 44*b*. Accordingly, the introduced exhaust gas EGI flows through the internal space K of the protector 45 (i.e., through the internal subspaces K1, K2, K3, K4, and K5 in this order), and reaches the gas discharge opening 45O.

In this manner, a portion of the exhaust gas EG flowing within the exhaust pipe EP is introduced into the protector 45 through the gas introduction openings 45I, and the exhaust gas EG introduced into the protector 45 (the introduced exhaust gas EGI) is discharged to the outside of the protector 45 through the gas discharge opening 45O.

Referring back to FIG. 2, in the particulate sensor 10 of the present embodiment, a ring-shaped insulating holder 173 formed of an electrically insulating material is disposed inside the inner tube 80 to be located on the rear end side GK of the metallic shell 50 (specifically, on the rear end side GK of the ceramic sleeve 56). This insulating holder 173 has an insertion hole 173*c* extending through the insulating holder 173 in the axial direction GH, and the sensor element 100 is inserted into the insertion hole 173*c*. Further, a third insulating member 172 is disposed on the rear end side GK of the insulating holder 173 to be located adjacent to the insulating holder 173. This third insulating member 172 is formed of an electrically insulating material and has the shape of a tube extending in the axial direction GH.

Further, a first insulating member 71 is disposed inside the third insulating member 172. This first insulating member 71 is formed of an electrically insulating material and has the shape of a tube extending in the axial direction GH. Further, a second insulating member 72 is disposed on the rear end side GK of the first insulating member 71. This second insulating member 72 is formed of an electrically insulating material and has the shape of a tube extending in the axial direction GH. A cylindrical spacer 78 extending in the axial direction GH is disposed between the first and second insulating members 71 and 72.

The first insulating member 71 has an insertion hole 71*c* which penetrates the first insulating member 71 in the axial direction GH. The sensor element 100 extends through the insertion hole 71*c*, and a discharge potential terminal member 73 is accommodated in the insertion hole 71*c*. The second insulating member 72 has a first insertion hole 72*c* and a second insertion hole 72*d* which penetrate the second insulating member 72 in the axial direction GH (see FIG. 4). A rear end portion 100K of the sensor element 100 is located in the second insertion hole 72*d*, and a first heater terminal member 76 and a second heater terminal member 77 which will be described later are accommodated in the second insertion hole 72*b* in a mutually insulated state.

Notably, within the insertion hole 71*c*, the first insulating member 71 holds the discharge potential terminal member 73 while bringing it into electrical contact with a discharge potential pad 113 (see FIG. 7) of the sensor element 100. In addition, the first insulating member 71 electrically insulates the discharge potential terminal member 73 and the inner tube 80 from each other.

Also, within the second insertion hole 72*d*, the second insulating member 72 holds the first heater terminal member 76 while bringing it into electrical contact with a first heater pad 136 of the sensor element 100. Further, within the second insertion hole 72*d*, the second insulating member 72 holds the second heater terminal member 77 while bringing it into electrical contact with a second heater pad 137 of the sensor element 100. In addition, the second insulating member 72 electrically insulates the first heater terminal member 76 and the second heater terminal member 77 from a sensor GND metal connection member 82 (a tubular member connected to a rear end portion 80*k* of the inner tube 80).

The discharge potential lead wire 161 is inserted into the first insertion hole 72*c* of the second insulating member 72. One end portion 161*t* of the discharge potential lead wire 161 is connected to the discharge potential terminal member 73. As a result, the discharge potential terminal member 73 is maintained at the discharge potential PV2, and the discharge potential pad 113 connected to the discharge potential terminal member 73 is also maintained at the discharge potential PV2.

Further, within the second insertion hole 72*d*, the first heater terminal member 76 is connected to one end portion 163*t* of the first heater lead wire 163. As a result, the first heater terminal member 76 is maintained at the first heater potential PVht, and the first heater pad 136 connected to the first heater terminal member 76 is also maintained at the first heater potential PVht.

Further, within the second insertion hole 72*d*, the second heater terminal member 77 is connected to one end portion 164*t* of the second heater lead wire 164. As a result, the second heater terminal member 77 is maintained at the chassis GND potential CGND, and the second heater pad 137 connected to the second heater terminal member 77 is also maintained at the chassis GND potential CGND.

A forward end portion 82*s* of the tubular sensor GND metal connection member 82 is fitted onto the rear end portion 80*k* of the inner tube 80, and is laser-welded thereto. The sensor GND metal connection member 82 surrounds the circumferences of the first and second insulating members 71 and 72 (more specifically, the circumference of the third insulating member 172 which accommodates and holds the first and second insulating members 71 and 72). A rear end portion 82*k* of the sensor GND metal connection member 82 is crimped toward the radially inner side, to thereby support the second insulating member 72 located on the radially inner side thereof.

The inner external conductor 165G1 of the double external conductor 165G of the electric wire 165 electrically communicates with the sensor GND metal connection member 82 through a first connection member 99. As shown in FIG. 4, the first connection member 99 has a gripping portion 99*b* which receives and grips the inner external conductor 165G1, and an extension portion 99*c* extending from the gripping portion 99*b* toward the forward end side GS. The gripping portion 99*b* includes a tubular portion 99*d* which has a generally tubular shape and has a break at one location in the circumferential direction, and a pair of flat portions 99*f* which extend in parallel from the tubular portion 99*d* at the location of the break such that the flat portions 99*f* are spaced from each other. The pair of flat portions 99*f* have holes through which a shaft portion 98*b* of a rivet 98 is inserted. In a state in which the external conductor 165G1 is inserted into the tubular portion 99*d* of the gripping portion 99*b*, the shaft portion 98*b* of the rivet 98 inserted through the holes of the pair of flat portions 99*f* is crimped so as to tighten the pair of flat portions 99*f* (cause the pair of flat portions 99*f* to approach each other). As a result, it is possible to bring the tubular portion 99*d* into close contact with the external conductor 165G1 while reducing the diameter of the tubular portion 99*d*. In this manner, the external conductor 165G1 can be gripped by the gripping portion 99*b*.

In a state in which the external conductor 165G1 is gripped by the gripping portion 99b as described above, a forward end portion 99s of the extension portion 99c of the first connection member 99 is connected to the rear end portion 82k of the sensor GND metal connection member 82, so that the external conductor 165G1 electrically communicates with the sensor GND metal connection member 82. As a result, all the inner tube 80, the metallic shell 50, and the protector 45, which electrically communicate with the sensor GND metal connection member 82, are maintained at the sensor GND potential SGND.

A tubular member 85 formed of metal is fitted into and welded to a smaller-diameter portion 96 of the outer tube 95 on the rear end side GK. Further, a grommet 84 formed of fluororubber is disposed inside the tubular member 85. The electric wires 165, 167, and 168 extend through a through hole of the grommet 84. Notably, an 0 ring 86 is interposed between the smaller-diameter portion 96 of the outer tube 95 and the tubular member 85.

The outer external conductor 165G2 of the double external conductor 165G of the electric wire 165 electrically communicates with the outer tube 95 through a gripping member 89 and a third connection member 87. As shown in FIG. 4, the gripping member 89 includes a tubular portion 89d which has a generally tubular shape and has a break at one location in the circumferential direction, and a pair of flat portions 89f which extend in parallel from the tubular portion 89d at the location of the break such that the flat portions 89f are spaced from each other. The pair of flat portions 89f have holes through which a shaft portion 88b of a rivet 88 is inserted.

As shown in FIG. 4, the third connection member 87 has a flat contact portion 87b with which the flat portions 89f of the gripping member 89 are brought into contact, and a pair of flat extension portions 87c and 87d formed by bending opposite end portions of the contact portion 87b. The contact portion 87b has a hole through which the shaft portion 88b of the rivet 88 is inserted. The extension portions 87c and 87d are portions to be connected to the inner circumferential surface of the outer tube 95.

In a state in which the external conductor 165G2 is inserted into the tubular portion 89d of the gripping member 89 and the flat portions 89f of the gripping member 89 are in contact with the contact portion 87b of the third connection member 87, the shaft portion 88b of the rivet 88 inserted through the holes of the pair of flat portions 89f and the hole of the contact portion 87b is crimped so as to tighten the pair of flat portions 89f (cause the pair of flat portions 89f to approach each other). As a result, it is possible to bring the tubular portion 89d into close contact with the external conductor 165G2 while reducing the diameter of the tubular portion 89d. In this manner, the external conductor 165G2 can be gripped by the gripping member 89, and the gripping member 89 can be connected (coupled) to the third connection member 87.

The extension portions 87c and 87d of the third connection member 87 are connected to the inner circumferential surface of the outer tube 95, so that the external conductor 165G2 electrically communicates with the outer tube 95. As a result, all the outer tube 95, the mounting metallic member 90 electrically communicating the outer tube 95, and the exhaust pipe EP are maintained at the chassis GND potential CGND which is insulated from the sensor GND potential SGND. Notably, as described above, the chassis GND potential CGND is the same as the GND potential of the battery BT (see FIG. 6) mounted on the vehicle AM.

Figure 7:
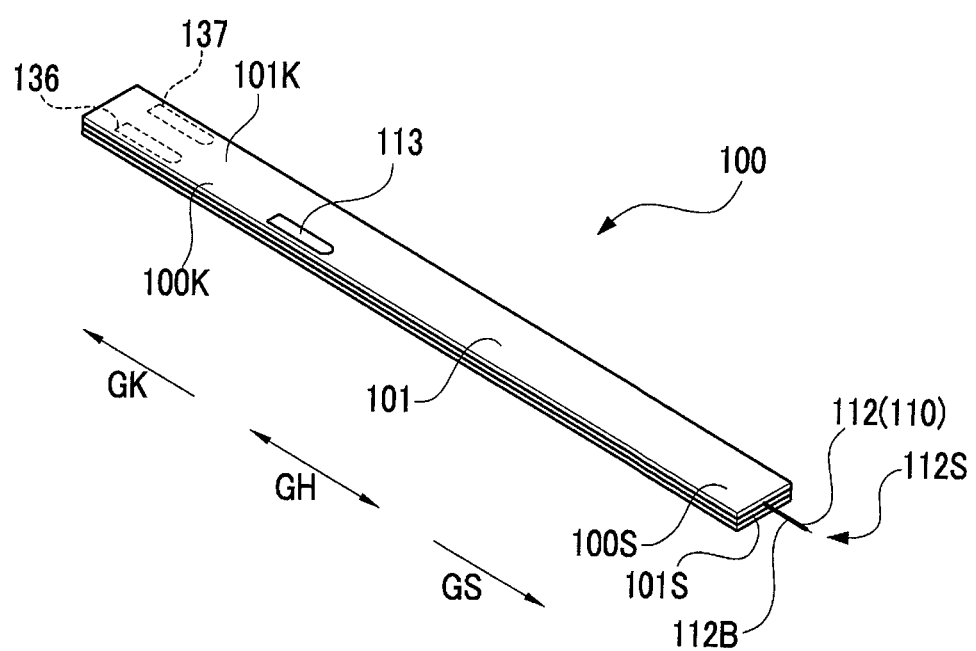
FIG. 7 is a perspective view of a sensor element which constitutes the particulate sensor.
Figure 8:
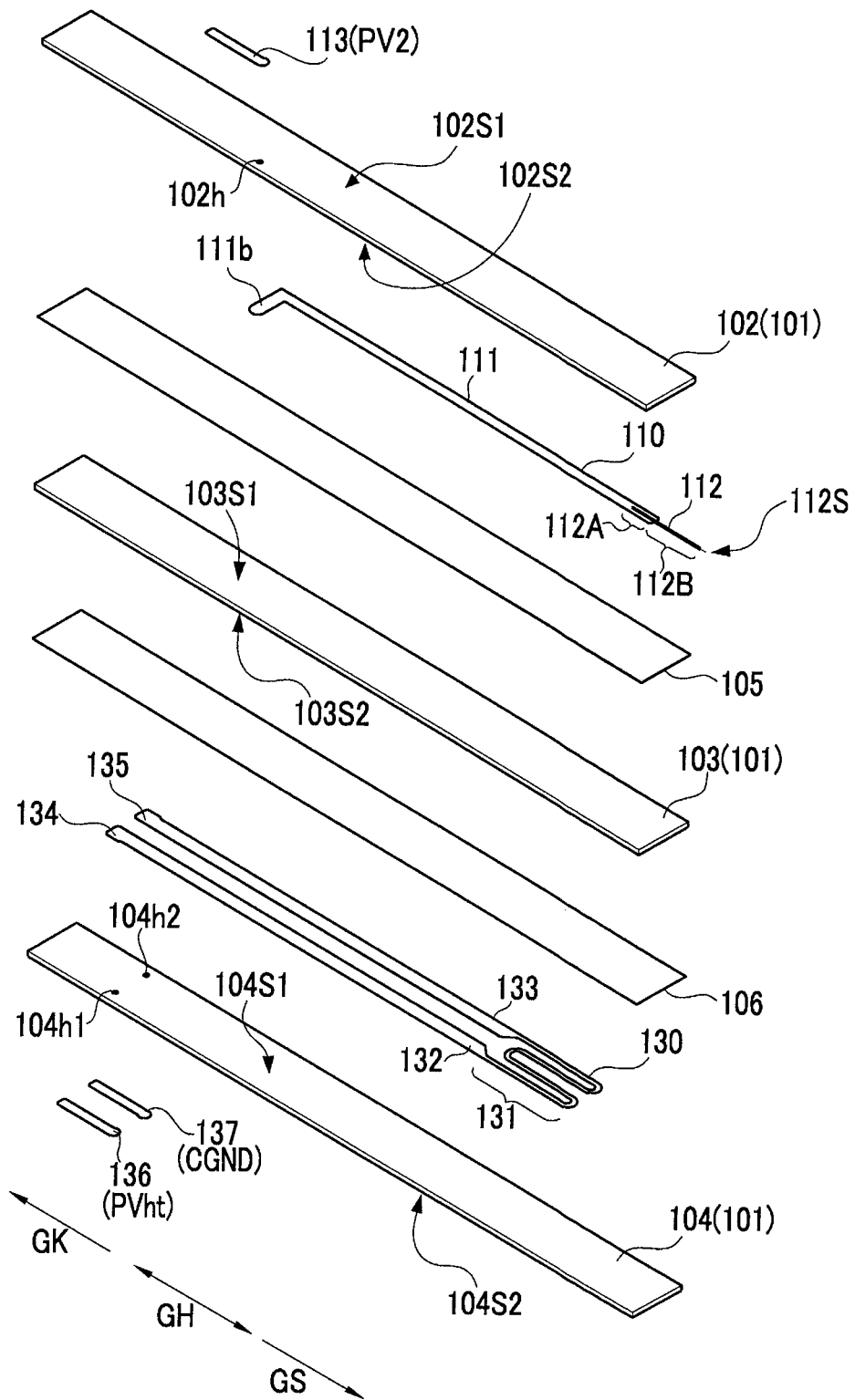
FIG. 8 is an exploded perspective view of the sensor element.

Next, the sensor element 100 will be described in detail. As shown in FIGS. 7 and 8, the sensor element 100 has a plate-shaped ceramic substrate 101 which extends in the axial direction GH and is formed of an electrically insulating material (specifically, alumina). The discharge electrode member 110 and the heater 130 are embedded in the ceramic substrate 101, and are integrated through firing (integral firing).

More specifically, the ceramic substrate 101 is a ceramic laminate in which three plate-shaped ceramic layers 102, 103, and 104 formed of alumina originating from an alumina green sheet are layered together. An insulating cover layer 105 formed from alumina through printing is present between the ceramic layers 102 and 103. The discharge electrode member 110 is disposed between the ceramic layer 102 and the insulating cover layer 105. Further, an insulating cover layer 106 formed from alumina through printing is present between the ceramic layers 103 and 104. The heater 130 is disposed between the insulating cover layer 106 and the ceramic layer 104. The layers, the member, and the heater are integrated together, whereby the sensor element 100 is formed.

The discharge electrode member 110 extends in the axial direction GH. The discharge electrode member 110 has a needle-shaped electrode portion 112 formed of platinum wire, and a lead portion 111 electrically communicating with the needle-shaped electrode portion 112. Notably, the lead portion 111 is formed on a second surface 102S2 of the ceramic layer 102 by means of pattern printing. The lead portion 111 of the discharge electrode member 110 and an embedment portion 112A (on the rear end side GK) of the needle-shaped electrode portion 112 are embedded in the ceramic substrate 101 (specifically, between the ceramic layer 102 and the ceramic layer 103). An end portion 111b of the lead portion 111 on the rear end side GK electrically commutates with the discharge potential pad 113 formed on a first surface 102S1 of the ceramic layer 102 through a through hole conductor formed in a through hole 102h extending through the ceramic layer 102.

Meanwhile, a portion of the needle-shaped electrode portion 112 on the forward end side GS serves as an exposed portion 112B which projects toward the forward end side GS from the forward end 101S of the ceramic substrate 101 to thereby be exposed to the outside of the ceramic substrate 101 (see FIG. 7). A portion of the exposed portion 112B on the forward end side GS forms a tapered needle-shaped distal end portion 112S.

Also, the heater 130 is formed on a first surface 104S1 of the ceramic layer 104 by means of pattern printing. The heater 130 has a heat generation portion 131 which is disposed on the forward end side GS of the sensor element 100, and two heater lead portions (a first heater lead portion 132 and a second heater lead portion 133) electrically communicating with the heat generation portion 131 and extending toward the rear end side GK of the sensor element 100. The heater 130 is formed on the first surface 104S1 of the ceramic layer 104, and is covered by the insulating cover layer 106. As a result, the heater 130 (the heat generation portion 131, the first heater lead portion 132, and the second heater lead portion 133) is embedded in the ceramic substrate 101 (specifically, between the ceramic layer 103 and the ceramic layer 104).

An end portion 134 of the first heater lead portion 132 on the rear end side GK electrically commutates with the first heater pad 136 formed on a second surface 104S2 of the ceramic layer 104 through a through hole conductor formed in a through hole 104h1 extending through the ceramic layer 104. An end portion 135 of the second heater lead portion 133 on the rear end side GK electrically commutates with the second heater pad 137 formed on the second surface 104S2 of the ceramic layer 104 through a through hole conductor formed in a through hole 104h2 extending through the ceramic layer 104.

Next, the electrical function and operation of the particulate detection system 1 will be described.

The discharge electrode member 110 of the sensor element 100 is connected to the ion source power supply circuit 210 of the control apparatus 200 through the discharge potential lead wire 161 (see FIG. 6). The heater 130 is connected to the heater energization circuit 226 of the control apparatus 200 through the first and second heater lead wires 163 and 164.

The inner external conductor 165G1 of the electric wire 165 is connected to the first output terminal 211 of the ion source power supply circuit 210 in the control apparatus 200, whereby the inner external conductor 165G1 is maintained at the sensor GND potential SGND. Further, the protector 45 disposed around the sensor element 100 is also maintained at the sensor GND potential SGND through the sensor GND metal connection member 82, etc. electrically communicating with the external conductor 165G1.

The discharge potential PV2, which is a positive high voltage (e.g., 1 to 2 kV), is supplied from the ion source power supply circuit 210 to the needle-shaped electrode portion 112 of the discharge electrode member 110 through the discharge potential lead wire 161, the discharge potential terminal member 73, and the discharge potential pad 113. As a result, gaseous discharge (specifically, corona discharge) occurs between the exposed portion 112B of the needle-shaped electrode portion 112 and the protector 45 (the gas introduction pipe) maintained at the sensor GND potential SGND, whereby ions CP (positive ions) are generated around the exposed portion 112B (in particular, near the forward end 110s of the discharge electrode member 110 (see FIG. 9).

As described above, the exhaust gas EG is introduced into the interior of the protector 45 through the gas introduction openings 45I. Therefore, as shown in FIG. 9, the ions CP generated around the exposed portion 112B adhere to the particulates S contained in the introduced exhaust gas EGI. As a result, the particulates S become positively electrified particulates SC. Since a flow of the introduced exhaust gas EGI from the rear end side GK toward the forward end side GS is produced within the protector 45, the electrified particulates SC flow toward the gas discharge opening 45O together with the introduced exhaust gas EGI, and are discharged to the outside of the protector 45 through the gas discharge opening 45O. Accordingly, the electrified particulates SC are discharged from the interior of the protector 45 into the exhaust pipe EP through the gas discharge opening 45O as particulates containing discharged ions CPH.

In the present system 1, a signal (signal current Is) corresponding to the amount of charge of the discharged ions CPH discharged through the gas discharge opening 45O is detected by the signal current detection circuit 230. Notably, the signal current Is flows between the sensor GND potential SGND (the potential of the protector 45, etc.) and the chassis GND potential CGND (the potential of the exhaust pipe EP, etc.) As a result, the amount (concentration) of the particulates S contained in the exhaust gas EG can be detected.

Notably, as described above, in the present embodiment, the protector 45 disposed around the sensor element 100 is maintained at the sensor GND potential SGND, and corona discharge is generated between the protector 45 and the exposed portion 112B of the discharge electrode member 110. Additionally, the protector 45 is also used as a collection electrode for collecting floating ions CPF. Namely, in the present embodiment, the collection potential for collecting the floating ions CPF by the protector 45 (collection electrode) is equal to the sensor GND potential SGND.

In the present system 1, when the heater energization circuit 226 of the measurement control circuit 220 of the control apparatus 200 supplies electricity to the heater 130 through the first heater pad 136 and the second heater pad 137 (applies a predetermined heater energization voltage between the first heater pad 136 and the second heater pad 137), the heat generation portion 131 of the heater 130 generates heat, whereby the sensor element 100 can be heated. As a result, foreign substances adhering to the sensor element 100 can be removed.

Notably, in the present embodiment, a voltage obtained from the DC battery voltage (DC 12 V or 24 V) of the battery BT of the vehicle AM through pulse control performed by the heater energization circuit 226 is applied as the heater energization voltage. Specifically, the first heater potential PVht which is applied to the first heater pad 136 through the first heater lead wire 163 and the first heater terminal member 76 is a positive side potential obtained as a result of the pulse control of the battery voltage (DC 12 V or 24 V). Also, the second heater potential which is applied to the second heater pad 137 through the second heater lead wire 164 and the second heater terminal member 77 is the chassis GND potential CGND which is the same as the GND potential of the battery BT (see FIG. 6).

Incidentally, unlike the conventional particulate sensor, the particulate sensor 10 of the present embodiment does not have an auxiliary electrode member which applies to the floating ions CPF a repulsive force toward the gas introduction pipe (protector) to thereby assist the collection of the floating ions CPF by the gas introduction pipe. Since a power supply circuit for supplying electric power to the auxiliary electrode member, a cable for connecting the power supply circuit to the auxiliary electrode member, etc. can be eliminated as a result of elimination of the auxiliary electrode member, the configuration of the particulate sensor can be simplified, and the production cost of the particulate sensor can be decreased. Also, through elimination of the auxiliary electrode member, the amount of electric power used in the particulate sensor can be decreased.

However, in the case where the auxiliary electrode member is removed from the conventional particulate sensor, the floating ions become more likely to be discharged to the outside of the gas introduction pipe through the gas discharge opening. Specifically, ions which have been produced near the forward end of the discharge electrode member but which have failed to adhere to the particulates tend to flow, as floating ions, toward the gas discharge opening; i.e., toward the forward end side in the axial direction. Therefore, the amount of floating ions which reach the gas discharge opening without hitting against (adhering to) the gas introduction pipe may increase, and the amount of floating ions which cannot be collected by the gas introduction pipe may increase. Namely, there may be increased the amount of floating ions which are discharged, together with the electrified particulates, to the outside of the gas introduction pipe through the gas discharge opening.

Incidentally, if floating ions are discharged, together with electrified particulates, to the outside of the gas introduction pipe through the gas discharge opening, the signal current flows in accordance with the sum of the amount of the ions contained in the electrified particulates and the amount of the floating ions. Namely, the magnitude of the detected signal current deviates (has an offset) from the magnitude of the signal current flowing in accordance with the amount of ions contained in the electrified particulates discharged to the outside of the gas introduction pipe through the gas discharge opening, by an amount corresponding to the magnitude of the signal current flowing in accordance with the amount of floating ions discharged to the outside of the gas introduction pipe through the gas discharge opening. Accordingly, there is produced a detection error corresponding to the magnitude of the signal current flowing in accordance with the amount of floating ions discharged to the outside of the gas introduction pipe through the gas discharge opening. Therefore, if the auxiliary electrode member is removed from the conventional particulate sensor, there arises a possibility that the amount of floating ions discharged to the outside of the gas introduction pipe through the gas discharge opening increases, and the accuracy of particulate detection decreases.

In contrast, in the particulate sensor 10 of the present embodiment, as described above, the collection member 40 connected to the protector 45 (the gas introduction pipe) to thereby be maintained at the collection potential (the sensor GND potential SGND) is disposed inside the protector 45. The collection member 40 is disposed in the interior (the internal space K) of the protector 45 to be located between the forward end 110s of the discharge electrode member 110 and the gas discharge opening 45O such that the forward end 110s of the discharge electrode member 110 cannot be visually recognized from the outside of the protector 45 through the gas discharge opening 45O (see FIGS. 10 and 11). In other words, the collection member 40 is disposed in the internal space K of the protector 45 to be located between the forward end 110s of the discharge electrode member 110 and the gas discharge opening 45O such that the collection member 40 intersects with all straight lines (line segments) which connect the forward end 110s of the discharge electrode member 110 and the gas discharge opening 45O.

Notably, in the preset embodiment, the plate-shaped portion 43b of the collection member 40 prevents the forward end 110s of the discharge electrode member 110 from being visually recognized from the outside of the protector 45 through the gas discharge opening 45O. The all straight lines (line segments) which connect the forward end 110s of the discharge electrode member 110 and the gas discharge opening 45O are contained in a cone M represented by broken lines in FIGS. 10 and 11 (a cone whose bottom surface coincides with the gas discharge opening 45O and whose apex coincides with the forward end 110s of the discharge electrode member 110). From the positional relation between the cone M and the collection member 40, it is understood that the collection member 40 is disposed to intersect with all the straight lines (line segments) which connect the forward end 110s of the discharge electrode member 110 and the gas discharge opening 45O.

Therefore, even when the floating ions CPF (the ions CP that have been produced near the forward end 110s of the discharge electrode member 110 but which have failed to adhere to the particulates S) cannot be caused to hit against (adhere to) the protector 45 while flowing toward the gas discharge opening 45O, at least a portion of the floating ions CPF can be caused to hit against (adhere to) the collection member 40 and be collected by the collection member 40.

Accordingly, in the particulate sensor 10 of the present embodiment, the amount of the floating ions CPF which are discharged from the interior of the protector 45 (the gas introduction pipe) to the outside together with the electrified particulates SC can be reduced without provision of an auxiliary electrode member. As a result, in the particulate sensor 10 of the present embodiment, since the signal current Is which flows in accordance with the amount of the floating ions CPF discharged from the interior of the protector 45 to the outside can be decreased, the particulate detection accuracy can be improved.

Incidentally, in the particulate sensor 10 of the present embodiment, the gas discharge opening 45O is located at the forward end of the protector 45 (the gas introduction pipe) and is open in the axial direction GH. Also, within the protector 45, the forward end 110s of the discharge electrode member 110 is located within a cylindrical region TA surrounded by an imaginary tube T which extends from the perimeter (peripheral edge) of the gas discharge opening 45O toward the rear end side GK in the axial direction GH (a cylinder represented by two-dot chain lines in FIGS. 10 and 11) (see FIGS. 10 and 11). In such a particulate sensor, at least a portion of the floating ions CPF (the ions CP that have been produced near the forward end 110s of the discharge electrode member 110 but which have failed to adhere to the particulates S) flows toward the forward end side GS in the axial direction GH; i.e., toward the gas discharge opening 45O.

In contrast, in the particulate sensor 10 of the present embodiment, the collection member 40 is disposed at a position where the collection member 40 intersects all the straight lines which extend in the axial direction GH through the gas discharge opening 45O (see FIGS. 10 and 11). Therefore, even when the floating ions CPF which flow toward the forward end side GS in the axial direction GH; i.e., toward the gas discharge opening 45O, cannot be caused to hit against (adhere to) the protector 45 (the gas introduction pipe) for collection thereof, the floating ions CPF can be caused to hit against (adhere to) the collection member 40 and be collected by the collection member 40.

Notably, all the straight lines which extend in the axial direction GH through the gas discharge opening 45O are contained in the cylindrical region TA. From the positional relation between the cylindrical region TA and the collection member 40, it is understood that the collection member 40 is disposed at a position where the collection member 40 intersects with all the straight lines which extend in the axial direction GH through the gas discharge opening 45O.

Further, in the particulate sensor 10 of the present embodiment, the collection member 40 has a plurality (four in the present embodiment) of plate-shaped portions 41b to 44b which are arranged at predetermined intervals in the axial direction GH so as to divide the internal space K of the protector 45 (the gas introduction pipe) in the axial direction GH. Accordingly, the internal space K of the protector 45 is divided into a plurality (five in the present embodiment) of the internal subspaces K1 to K5 arranged in the axial direction GH by the plurality (four) of plate-shaped portions 41b to 44b spaced from one another in the axial direction GH. Further, each of the plate-shaped portions 41b to 44b has the through hole(s) (41d to 44d) penetrating therethrough in the axial direction GH.

Accordingly, each of the plate-shaped portions 41b to 44b can guide (cause) the gas under measurement (introduced exhaust gas EGI) containing the electrified particulates SC and the floating ions CPF to flow, through its through hole 41d to 44d, from the internal subspace (K1, K2, K3, or K4) located on the rear end side GK of the plate-shaped portion (41b, 42b, 43b, or 44b) to the internal subspace (K2, K3, K4, or K5) located on the forward end side GS of the plate-shaped portion (41b, 42b, 43b, or 44b). Accordingly, the introduced exhaust gas EGI containing the electrified particulates SC and the floating ions CPF flows within the collection member 40 while passing through the through holes 41d, 42d, 43d, and 44d of the plate-shaped portions 41b, 42b, 43b, and 44b. Accordingly, the introduced exhaust gas EGI flows through the internal space K of the protector 45 (i.e., through the internal subspaces K1, K2, K3, K4, and K5 in this order).

Further, in the particulate sensor 10 of the present embodiment, the through holes (41d to 44d) of the plate-shaped portions (41b to 44b) located adjacent to each other in the axial direction GH are formed at positions determined such that the through hole(s) of one of the plate-shaped portions does not overlap with the through hole(s) of the other of the plate-shaped portions as viewed in the axial direction GH (see FIG. 5 and FIGS. 9 to 11). Specifically, the plate-shaped portions 41b to 44b are disposed to be coaxial with one another, and the plate-shaped portion 41b located closest to the rear end side GK has the plurality of through holes 41d formed in a peripheral edge portion thereof. Meanwhile, the plate-shaped portion 42b located adjacent to the plate-shaped portion 41b has the single through hole 42d which is formed at the center thereof (position which does not overlap with the through holes 41d of the plate-shaped portion 41b as viewed in the axial direction GH). Further, the plate-shaped portion 43b which is located on the forward end side GS of the plate-shaped portion 42b and is located adjacent to the plate-shaped portion 42b has the plurality of through holes 43d which are formed in a peripheral edge portion thereof (position which does not overlap with the through hole 42d of the plate-shaped portion 42b as viewed in the axial direction GH). Further, the plate-shaped portion 44b which is located on the forward end side GS of the plate-shaped portion 43b and is located adjacent to the plate-shaped portion 43b has the single through hole 44d which is formed at the center thereof (position which does not overlap with the through holes 43d of the plate-shaped portion 43b as viewed in the axial direction GH).

Since the collection member 40 has such a structure, for example, when the floating ions CPF flow, through the through holes 41d of the plate-shaped portion 41b located closest to the rear end side GK in the axial direction GH, from the internal subspace K1 located on the rear end side GK of the plate-shaped portion 41b to the internal subspace K2 located on the forward end side GS of the plate-shaped portion 41b, the plate-shaped portion 42b (a portion thereof where the through hole 42d is not formed) adjacently located on the forward end side GS of the plate-shaped portion 41b is present in a region to which the floating ions CPF flow (i.e., in a direction in which the floating ions CPF advance). Therefore, the floating ions CPF having passed through the through holes 41d of the plate-shaped portion 41b become more likely to hit against (adhere to) the plate-shaped portion 42b adjacently located on the forward end side GS of the plate-shaped portion 41b (see FIG. 9). The same is true of the remaining plate-shaped portions 42b to 44b located adjacent to one another in the axial direction GH.

As described above, in the particulate sensor 10 of the present embodiment, the collection member 40 is configured such that the gas under measurement (the introduced exhaust gas EGI) containing the electrified particulates SC and the floating ions CPF can flow from the rear end side GK toward the forward end side GS through the through holes 41d to 44d of the plate-shaped portions 41b to 44b of the collection member 40, and the floating ions CPF are more likely to be collected by the collection member 40. Accordingly, the particulate sensor 10 of the present embodiment can further decrease the amount of the floating ions CPF discharged from the interior of the protector 45 (the gas introduction pipe) to the outside without providing an auxiliary electrode member.

Figure 9:
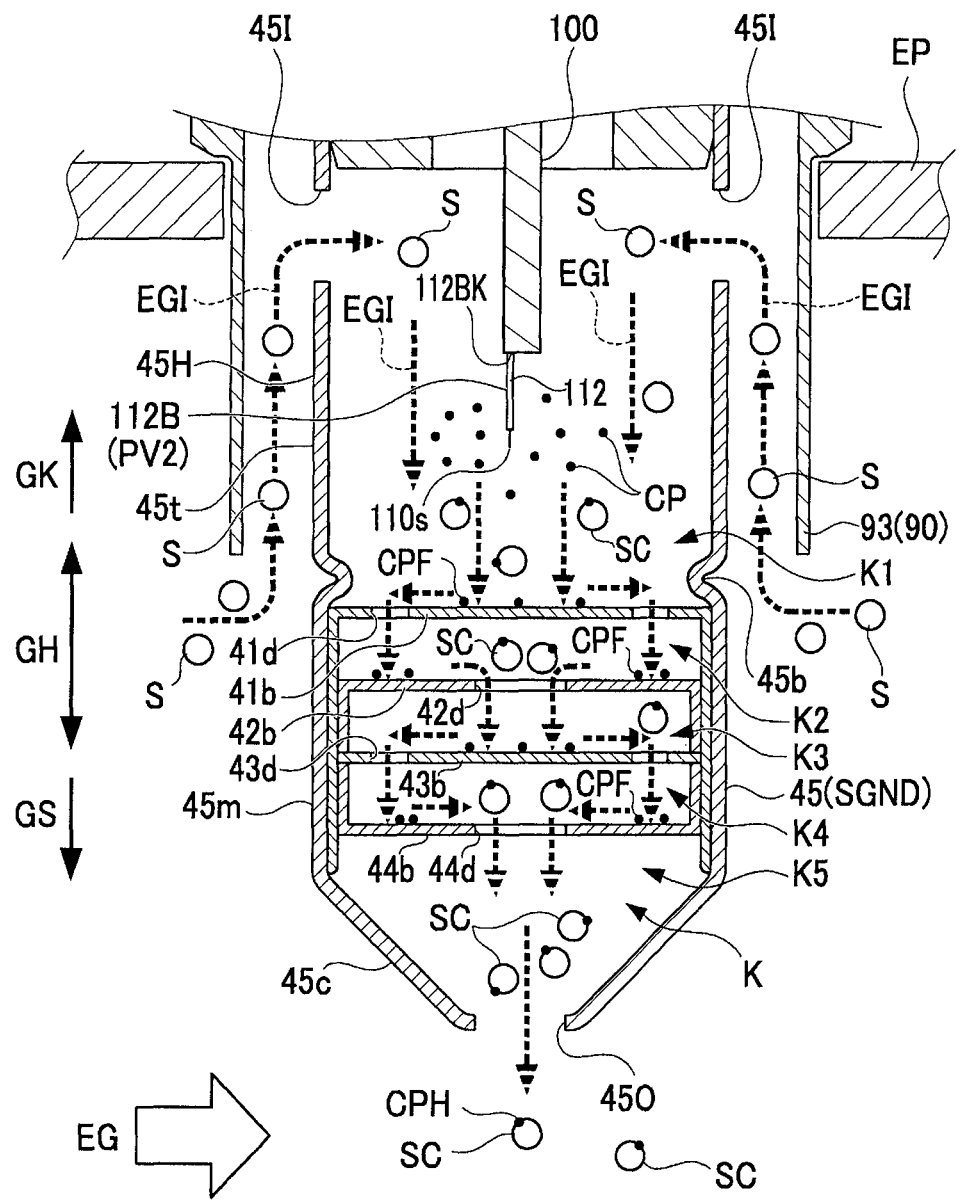
FIG. 9 is an explanatory view of the particulate detection system according to the embodiment.

Incidentally, in the particulate sensor 10 of the present embodiment, the entire gas introduction openings 45I of the protector 45 (the gas introduction pipe) are disposed on the rear end side GK in relation to the forward end 110s of the discharge electrode member 110 (further, on the rear end side GK in relation to the rear end 112BK of the exposed portion 112B) (see FIG. 9). Therefore, it becomes easier for the ions CP generated around the exposed portion 112B as a result of corona discharge (gaseous discharge) to adhere to the particulates S contained in the exhaust gas EG introduced into the interior of the protector 45 through the gas introduction openings 45I. Thus, the amount of the floating ions CPF can be decreased.

Figure 12:
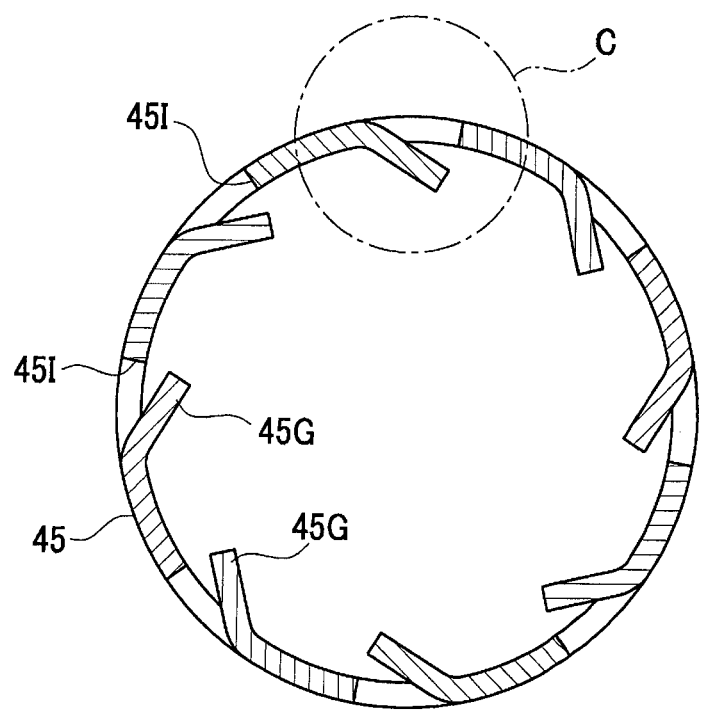
FIG. 12 is a transverse sectional view of a protector (a gas introduction pipe) of the particulate sensor.
Figure 13:
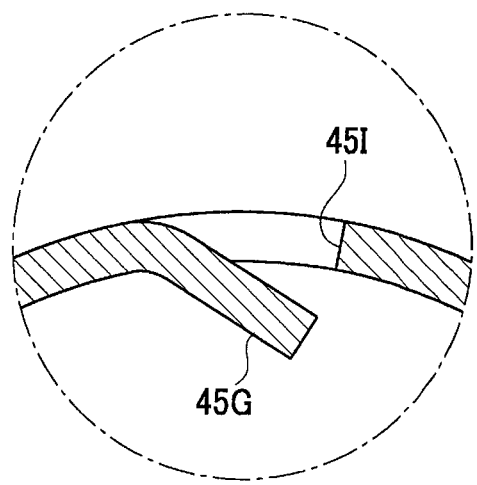
FIG. 13 is an enlarged view of portion C of FIG. 12.

Further, in the particulate sensor 10 of the present embodiment, as shown in FIGS. 12 and 13, guides 45G are provided at the gas introduction openings 45I of the protector 45. FIG. 12 is a sectional view of the protector 45 taken along line B-B of FIG. 2. FIG. 13 is an enlarged view of portion C of FIG. 12. The guides 45G have a shape for guiding the exhaust gas EG to the interior of the protector 45 such that the exhaust gas EG (the gas under measurement) introduced into the interior of the protector 45 through the gas introduction openings 45I swirls around the exposed portion 112B; i.e., forms a swirling flow around the exposed portion 112B.

Specifically, a portion of the cylindrical side wall of the protector 45 has squarish C-shaped slits each composed of two slits extending parallel in the circumferential direction and a slit extending in the axial direction GH and connecting the two slits together. Portions (portions which become the guides 45G) surrounded by the squarish C-shaped slits are bent toward the radially inner sides of the protector 45. As a result, the guides 45G are formed, and simultaneously, the gas introduction openings 45I are formed (see FIGS. 12 and 13). Each of the guides 45G extends from the side wall of the protector 45 in a direction orthogonal to the axial direction GH. Notably, in the present embodiment, the gas introduction openings 45I (the guides 45G) are provided at eight positions which are equally spaced from one another in the circumferential direction of the protector 45.

Accordingly, the guides 45G guide the exhaust gas EG to the interior of the protector 45, and the exhaust gas EG introduced into the interior of the protector 45 generates a swirling flow around the exposed portion 112B. As a result of generation of a swirling flow of the exhaust gas EG around the exposed portion 112B, the ions CP generated around the exposed portion 112B become more likely to come into contact with (adhere to) to the particulates S contained in the exhaust gas EG. Thus, the amount of the ions CP which adhere to the particulates S can be increased. As a result, the signal current Is which flows in accordance with the amount of the ions CP adhering to the particulates S (the amount of electric charge of the discharged ions CPH) can be increased, whereby the sensitivity of the particulate sensor 10 can be improved.

Also, as described above, the particulate sensor 10 of the present embodiment has the tubular wall portion 93 circumferentially surrounds the protector 45 (specifically, the rear tubular portion 45t of the protector 45 where the gas introduction openings 45I are formed) with an annular gap formed therebetween. As a results, the gas introduction openings 45I are covered by the tubular wall portion 93 from the outer side (the outer side in the radial direction of the protector 45) (see FIG. 9). Namely, when the protector 45 is viewed in the radial direction (the direction orthogonal to the axial direction GH) from the outside, the gas introduction openings 45I are located behind the tubular wall portion 93 and cannot be visually recognized. Therefore, when water (water droplets) is splashed from the outside of the protector 45 toward the gas introduction openings 45I, the tubular wall portion 93 prevents the water (water droplets) from entering the gas introduction openings 45I. As a result, water (water droplets) becomes unlikely to enter the interior of the protector 45 through the gas introduction openings 45I.

(Comparative Test on Floating Ion Discharge Amount)

A comparative test was carried out for the particulate sensor 10 of the embodiment and particulate sensors of comparative examples 1 and 2 so as to compare them in terms of the amount of the floating ions CPF discharged from the interior of the protector (the gas introduction pipe) to the outside through the gas discharge opening 45O.

The particulate sensor of comparative example 1 is the same as the particulate sensor 10 of the embodiment except the point that the particulate sensor of comparative example 1 does not have the collection member 40 and the point that the gas introduction openings of the protector of the particulate sensor of comparative example 1 differ in shape from that of the particulate sensor 10 of the embodiment. The protector of the particulate sensor of comparative example 1 has, as gas introduction openings, circular through holes which are formed in and penetrate the side wall of the protector at the same positions as the gas introduction openings 45I of the protector 45 of the embodiment, but does not have guides. The particulate sensor of comparative example 2 differs from the particulate sensor 10 of the embodiment only in the point that the particulate sensor of comparative example 2 does not have the collection member 40.

Specifically, the particulate sensor 10 was attached to an exhaust pipe (gas flow pipe) for test, air containing no particulate (soot, etc.) was supplied to the exhaust pipe, and the magnitude of the signal current Is detected by the signal current detection circuit 230 was grasped. Notably, in the present test, the flow speed of air discharged from the gas discharge opening 45O of the protector (gas discharge speed) was changed to different speeds by changing the flow speed of air supplied to the exhaust pipe, and the magnitude (pA) of the signal current Is was measured each time the gas discharge speed was changed to a different speed. The measurement was performed in the same manner for the particulate sensors of comparative examples 1 and 2.

In this test, air containing no particulate (soot, etc.) is supplied as the gas under measurement. Therefore, all the ions CP generated as a result of corona discharge are floating ions CPF, and all the ions CP discharged from the protector through the gas discharge opening 45O are floating ions CPF. Accordingly, it can be said that a particulate sensor whose signal current Is is larger as compared with other particulate sensors discharges a larger amount of the floating ions CPF from the interior of the protector (the gas introduction pipe) to the outside though the gas discharge opening 45O, as compared with other particulate sensors. In other words, it can be said that a particulate sensor whose signal current Is is smaller as compared with other particulate sensors can collect a greater amount of floating ions CPF within the protector (the gas introduction pipe), and can reduce more the amount of the floating ions CPF discharged from the interior of the protector to the outside, as compared with other particulate sensors.

Notably, the magnitude of the signal current Is detected in the present test is contained, as an offset (measurement error), in the signal current Is detected when measurement is performed by using exhaust gas containing particulates (soot, etc.) as the gas under measurement. Accordingly, when measurement is performed by using exhaust gas containing particulates (soot, etc.) as the gas under measurement, the signal current Is has a deviation (a detection error) corresponding to the magnitude of the offset, in relation to the magnitude of the signal current which flows in accordance with the amount of ions contained in the electrified particulates discharged to the outside of the gas introduction pipe through the gas discharge opening.

Figure 14:
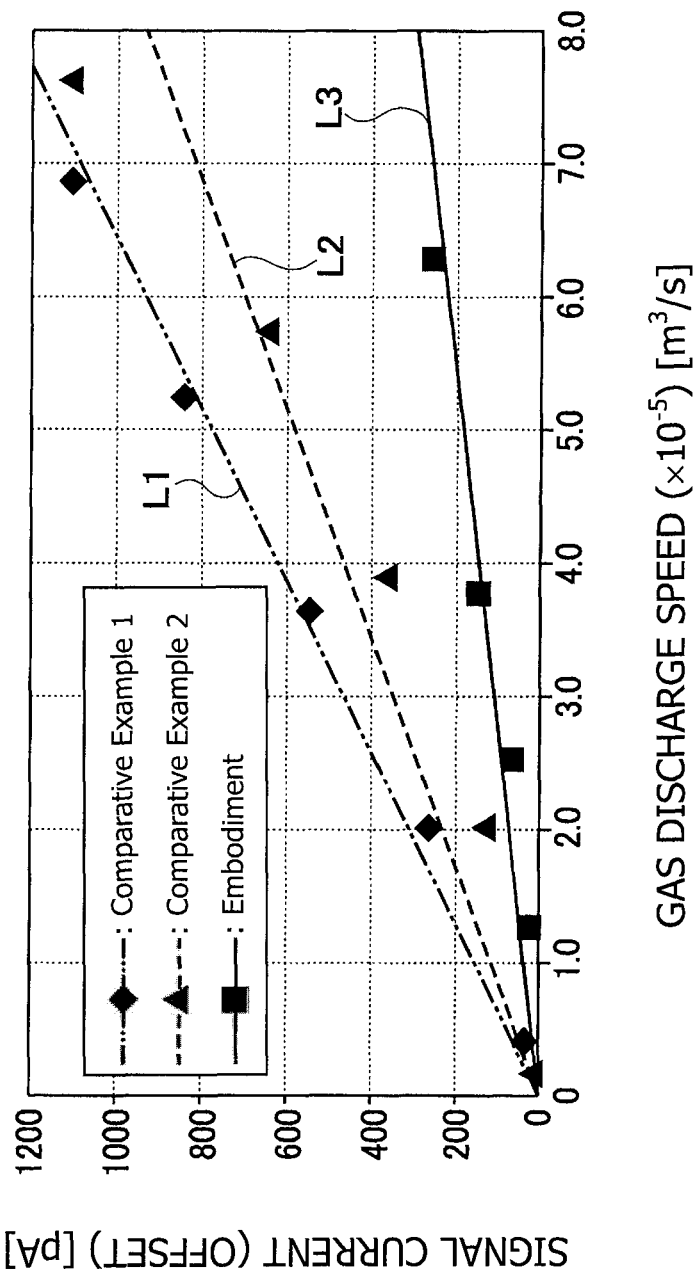
FIG. 14 is a graph showing the relation between gas discharge speed and the magnitude of signal current (offset).

FIG. 14 shows the results of the present test. FIG. 14 is a graph showing the relation between the gas discharge speed (the flow speed of the gas discharged from the gas discharge opening 45O of the protector) and the magnitude of the signal current Is (offset). In FIG. 14, data (measurement values) of the embodiment are plotted through use of square marks, data of comparative example 1 are plotted through use of rhombic marks, and data of comparative example 2 are plotted through use of triangular marks. Also, in FIG. 14, a regression line L1 (correlation line) obtained for the data of comparative example 1 by least square is represented by a two-dot chain line; a regression line L2 (correlation line) obtained for the data of comparative example 2 by least square is represented by a broken line; and a regression line L3 (correlation line) obtained for the data of the embodiment by least square is represented by a continuous line.

As can be understood from FIG. 14, in the case where the gas discharge speed is rendered approximately the same among the sensors, in the particulate sensor 10 of the embodiment, the signal current Is becomes smaller as compared with the particulate sensors of comparative examples 1 and 2. More specifically, the gradient of the regression line L3 (correlation line) of the embodiment becomes equal to or less than one half of the gradients of the regression lines L1 and L2 (correlation lines) of comparative examples 1 and 2. The test results show that, as compared with the particulate sensors of comparative examples 1 and 2, the particulate sensor 10 of the embodiment can collect a greater amount of floating ions CPF within the protector (the gas introduction pipe) and can decrease the amount of floating ions CPF discharged from the interior of the protector 45 to the outside.

Accordingly, in the particulate sensor 10 of the embodiment, the signal current Is which flows in accordance with the amount of floating ions CPF discharged from the interior of the gas introduction pipe (the protector 45) to the outside can be reduced as compared with the particulate sensors of comparative examples 1 and 2. Therefore, the particulate sensor 10 of the embodiment can be said to have an improved particulate detection accuracy.

Notably, the reason why the particulate sensor 10 of the embodiment can reduce the amount of floating ions CPF discharged from the interior of the protector 45 to the outside as compared with the particulate sensor of comparative example 2 is that, unlike the particulate sensor of comparative example 2, the particulate sensor 10 of the embodiment has the collection member 40 provided inside the protector 45 and therefore can collect a grater amount of floating ions CPF within the protector 45.

Also, the reason why the particulate sensor of comparative example 2 can reduce the amount of floating ions CPF discharged from the interior of the protector 45 to the outside as compared with the particulate sensor of comparative example 1 is that, unlike the particulate sensor of comparative example 1, the particulate sensor of comparative example 2 has the guides 45G which are provided at the gas introduction openings 45I of the protector such that the gas introduced into the interior of the protector through the gas introduction openings 45I forms a swirling flow around the exposed portion 112B. It is considered that as a result of generation of such a swirling flow, the amount of floating ions CPF flowing toward the forward end side GS in the axial direction GH; i.e., toward the gas discharge opening 45O, without coming into contact with the inner surface of the protector 45, decreases, as compared with the particulate sensor of comparative example 1, whereby the amount of floating ions CPF coming into contact with (adhering to) the inner surface of the protector 45 increases.

In the above, the present invention has been described on the basis of the embodiment. However, needless to say, the present invention is not limited to the above-described embodiment, and may be modified freely without departing from the scope of the invention.

For example, in the above-described embodiment, a plate-shaped ceramic laminate in which a plurality of ceramic layers are stacked in the thickness direction is used as the ceramic substrate 101 which constitutes the sensor element 100.

However, the ceramic substrate is not limited to those having a plate-like shape, and may have a rectangular columnar shape, a hexagonal columnar shape, a circular columnar shape, or a circular tubular shape. Examples of the circular columnar or circular tubular ceramic substrate include a ceramic laminate formed by stacking a plurality of ceramic layers in such a manner that annular rings similar to the annual rings of a tree are formed, and a ceramic laminate formed by spirally winding one or a plurality of ceramic sheets in such a manner that a plurality of ceramic layers are layered in the radial direction.

In the above-described embodiment, the mounting metallic member 90 is configured such that its tubular wall portion 93 located on the forward end side GS is inserted into the exhaust pipe EP, whereby the outer circumference of the rear tubular portion 45t of the gas introduction pipe (the protector 45) is surrounded by the tubular wall portion 93. However, instead of employing the configuration in which the outer circumference of the rear tubular portion 45t of the protector 45 is surrounded by the tubular wall portion 93 (instead of inserting the tubular wall portion 93 into the exhaust pipe EP), a tubular member which surrounds the outer circumference of the gas introduction pipe (the protector 45) may be fixed to the forward end 50s of the metallic shell 50 together with the gas introduction pipe (the protector 45).

DESCRIPTION OF SYMBOLS AND REFERENCE NUMERALS

1: particulate detection system
10: particulate sensor
40: collection member
41b, 42b, 43b, 44b: plate-shaped portion
41d, 42d, 43d, 44d: through hole
45: protector (gas introduction pipe; collection electrode)
45I: gas introduction opening
45O: gas discharge opening
50: metallic shell
80: inner tube
90: mounting metallic member
95: outer tube
100: sensor element
101: ceramic substrate
110: discharge electrode member
110s: forward end of the discharge electrode member
112: needle-shaped electrode portion
112B: exposed portion
130: heater
200: control apparatus
ENG: engine (internal combustion engine)
EG: exhaust gas (gas under measurement)
EP: exhaust pipe (gas flow pipe)
CGND: chassis GND potential (ground potential)
SGND: sensor GND potential (collection potential)
PV2: discharge potential
S: particulate
SC: electrified particulate
CP: ion
CPF: floating ion
GS: forward end side (axial direction forward end side)
GK: rear end side (axial direction rear end side)
GH: axial direction
Is: signal current
K: internal space of the gas introduction pipe
T: imaginary tube
TA: cylindrical region

The invention claimed is:
1. A particulate sensor comprising:
a tubular gas introduction pipe extending from a rear end side to a forward end side in an axial direction; and
a discharge electrode member which is contained in the gas introduction pipe and produces ions by gaseous discharge, wherein
the gas introduction pipe has a gas introduction opening which is located on the rear end side of the gas introduction pipe and through which a target gas containing particulates is introduced into the gas introduction pipe, and a gas discharge opening which is located on the forward end side of the gas introduction pipe and through which the target gas is discharged to an outside of the gas introduction pipe,
the discharge electrode member is located on the rear end side with respect to the gas discharge opening,
the gas introduction pipe contains the ions produced by the gaseous discharge, which adhere to the particulates contained in the target gas to generate electrified particulates,
the particulate sensor detects the particulates contained in the target gas by using a signal current flowing in accordance with the amount of the ions contained in the electrified particulates, which is discharged to the outside of the gas introduction pipe through the gas discharge opening,
the gas introduction pipe is maintained at a collection potential and serves as a collection electrode that collects floating ions which do not adhere to the particulates,
the particulate sensor does not have an auxiliary electrode member which applies to the floating ions a repulsive force toward the gas introduction pipe to thereby assist the collection of the floating ions by the gas introduction pipe, and has a collection member which is connected to the gas introduction pipe to thereby be maintained at the collection potential and is disposed between a forward end of the discharge electrode member and the gas discharge opening such that the forward end of the discharge electrode member cannot be visually recognized from the outside of the gas introduction pipe through the gas discharge opening, and the collection member is located entirely at a forward end side of the gas introduction opening in the axial direction.

2. The particulate sensor according to claim 1, wherein the gas discharge opening is open in the axial direction;

the forward end of the discharge electrode member is located within a cylindrical region of the gas introduction pipe which is surrounded by an imaginary tube formed by extending a perimeter of the gas discharge opening toward the rear end side in the axial direction; and the collection member is disposed at a position where the collection member intersects with all straight lines extending in the axial direction while passing through the gas discharge opening.

3. The particulate sensor according to claim 2, wherein the collection member includes a plurality of plate-shaped portions arranged at predetermined intervals in the axial direction such that the plate-shaped portions divide an internal space of the gas introduction pipe;

each plate-shaped portion has a through hole which penetrates the plate-shaped portion in the axial direction; and the through holes of the plate-shaped portions located adjacent to each other in the axial direction are formed such that the through hole of one of the plate-shaped portions does not overlap the through hole of the other plate-shaped portion as viewed in the axial direction.

4. The particulate sensor according to claim 2, wherein the particulate sensor is attached to a metallic gas flow pipe through which the target gas flows and which is maintained at a ground potential;

the gas introduction pipe is maintained at the collection potential different from the ground potential;

the discharge electrode member is maintained at a discharge potential different from the ground potential and the collection potential and generates the gaseous discharge between the discharge electrode member and the gas introduction pipe;

the gas discharge opening is disposed within the gas flow pipe; and the particulate sensor detects the amount of the particulates contained in the target gas by using the signal current flowing between the collection potential and the ground potential in proportion to the amount of the ions discharged from the gas introduction pipe into the gas flow pipe through the gas discharge opening.

5. The particulate sensor according to claim 1, wherein the particulate sensor is attached to a metallic gas flow pipe through which the target gas flows and which is maintained at a ground potential;

the gas introduction pipe is maintained at the collection potential different from the ground potential;

the discharge electrode member is maintained at a discharge potential different from the ground potential and the collection potential and generates the gaseous discharge between the discharge electrode member and the gas introduction pipe;

the gas discharge opening is disposed within the gas flow pipe; and the particulate sensor detects the amount of the particulates contained in the target gas by using the signal current flowing between the collection potential and the ground potential in proportion to the amount of the ions discharged from the the gas introduction pipe into the gas flow pipe through the gas discharge opening.

6. The particulate sensor according to claim 1, wherein all of straight lines which extend in the axial direction from the forward end of the discharge electrode member through the gas discharge opening are contained in the gas introduction pipe.

7. The particulate sensor according to claim 1, wherein the gas introduction opening is entirely disposed rearward from the discharge electrode member.

8. The particulate sensor according to claim 1, wherein the tubular gas introduction pipe has taper portion at a front end thereof.

9. A particulate sensor comprising:

a tubular gas introduction pipe extending from a rear end side to a forward end side in an axial direction; and a discharge electrode member which is contained in the gas introduction pipe and produces ions by gaseous discharge, wherein the gas introduction pipe has a gas introduction opening which is located on the rear end side of the gas introduction pipe and through which a target gas containing particulates is introduced into the gas introduction pipe, and a gas discharge opening which is located on the forward end side of the gas introduction pipe and through which the target gas is discharged to an outside of the gas introduction pipe, the discharge electrode member is located on the rear end side with respect to the gas discharge opening, the gas introduction pipe contains the ions produced by the gaseous discharge, which adhere to the particulates contained in the target gas to generate electrified particulates, the particulate sensor detects the particulates contained in the target gas by using a signal current flowing in accordance with the amount of the ions contained in the electrified particulates, which is discharged to the outside of the gas introduction pipe through the gas discharge opening, the gas introduction pipe is maintained at a collection potential and serves as a collection electrode that collects floating ions which do not adhere to the particulates, the particulate sensor does not have an auxiliary electrode member which applies to the floating ions a repulsive force toward the gas introduction pipe to thereby assist the collection of the floating ions by the gas introduction pipe, and has a collection member which is connected to the gas introduction pipe to thereby be maintained at the collection potential and is disposed between a forward end of the discharge electrode member and the gas discharge opening such that the forward end of the discharge electrode member cannot be visually recognized from the outside of the gas introduction pipe through the gas discharge opening, the collection member includes a plurality of plate-shaped portions arranged at predetermined intervals in the axial direction such that the plate-shaped portions divide an internal space of the gas introduction pipe, each plate-shaped portion has a through hole which penetrates the plate-shaped portion in the axial direction, and the through holes of the plate-shaped portions located adjacent to each other in the axial direction are formed such that the through hole of one of the plate-shaped portions does not overlap the through hole of the other plate-shaped portion as viewed in the axial direction.

10. The particulate sensor according to claim 9, wherein
the particulate sensor is attached to a metallic gas flow pipe through which the target gas flows and which is maintained at a ground potential;
the gas introduction pipe is maintained at the collection potential different from the ground potential;
the discharge electrode member is maintained at a discharge potential different from the ground potential and the collection potential and generates the gaseous discharge between the discharge electrode member and the gas introduction pipe;
the gas discharge opening is disposed within the gas flow pipe; and
the particulate sensor detects the amount of the particulates contained in the target gas by using the signal current flowing between the collection potential and the ground potential in proportion to the amount of the ions discharged from the gas introduction pipe into the gas flow pipe through the gas discharge opening.

* * * * *